(12) United States Patent
Sampson et al.

(10) Patent No.: US 11,672,524 B2
(45) Date of Patent: Jun. 13, 2023

(54) DEVICES AND METHODS FOR TETHER CUTTING

(71) Applicant: Ancora Heart, Inc., Santa Clara, CA (US)

(72) Inventors: Russel Sampson, Palo Alto, CA (US); David Scott Baron, Sunnyvale, CA (US); Rob Kotmel, Burlingame, CA (US)

(73) Assignee: Ancora Heart, Inc., Santa Clara, CA (US)

( * ) Notice: Subject to any disclaimer, the term of this patent is extended or adjusted under 35 U.S.C. 154(b) by 379 days.

(21) Appl. No.: 16/929,789

(22) Filed: Jul. 15, 2020

(65) Prior Publication Data

US 2021/0015478 A1 Jan. 21, 2021

Related U.S. Application Data

(60) Provisional application No. 62/874,279, filed on Jul. 15, 2019.

(51) Int. Cl.
*A61B 17/04* (2006.01)
*A61B 17/00* (2006.01)

(52) U.S. Cl.
CPC ............ *A61B 17/0467* (2013.01); *A61B 2017/00292* (2013.01); *A61B 2017/00367* (2013.01)

(58) Field of Classification Search
CPC ............ A61B 17/0467; A61B 17/0469; A61B 17/0485; A61B 2017/00477; A61B 2017/0474; A61B 2017/0469; A61B 17/0401; A61B 17/0057; A61B 17/0482
See application file for complete search history.

(56) References Cited

U.S. PATENT DOCUMENTS

| | | | |
|---|---|---|---|
| 2,108,206 | A | 2/1938 | Sidney |
| 2,618,137 | A | 11/1952 | White |
| 3,537,666 | A | 11/1970 | Lewis et al. |
| 3,656,185 | A | 4/1972 | Carpentier |
| 3,727,614 | A | 4/1973 | Kniazuk |

(Continued)

FOREIGN PATENT DOCUMENTS

| | | |
|---|---|---|
| EP | 0363661 A1 | 4/1990 |
| EP | 0637431 A1 | 2/1995 |

(Continued)

OTHER PUBLICATIONS

Co-pending U.S. Appl. No. 10/812,496, filed Mar. 29, 2004.

(Continued)

*Primary Examiner* — Tuan V Nguyen
(74) *Attorney, Agent, or Firm* — Cooley LLP

(57) ABSTRACT

Devices and methods for cutting a tether are described herein. Devices described herein generally comprise a proximal handle, a catheter, and an inner shaft and a cutting blade disposed within the lumen of the catheter, where the cutting blade is movably disposed over the inner shaft. The proximal handle comprises an actuation mechanism to control the movement of the components of the device. Methods described herein generally comprise advancing a tether-cutting device over a tether, loading the tether through the catheter and inner shaft, applying tension to the tether, and rotating and distally translating a cutting blade in order to cut the tether.

31 Claims, 14 Drawing Sheets

(56) References Cited

U.S. PATENT DOCUMENTS

| | | |
|---|---|---|
| 3,773,034 A | 11/1973 | Burns et al. |
| 3,837,345 A | 9/1974 | Matar |
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,169,303 A | 10/1979 | Lemelson |
| 4,273,127 A | 6/1981 | Auth et al. |
| 4,290,151 A | 9/1981 | Massana |
| 4,366,479 A | 12/1982 | Mori et al. |
| 4,373,923 A | 2/1983 | Kilwin |
| 4,384,406 A | 5/1983 | Tischlinger |
| 4,445,509 A | 5/1984 | Auth |
| 4,445,892 A | 5/1984 | Hussein et al. |
| 4,489,446 A | 12/1984 | Reed |
| 4,494,542 A | 1/1985 | Lee |
| 4,510,934 A | 4/1985 | Batra |
| 4,549,545 A | 10/1985 | Levy |
| 4,619,247 A | 10/1986 | Inoue et al. |
| 4,681,093 A | 7/1987 | Ono et al. |
| 4,700,250 A | 10/1987 | Kuriyama |
| 4,705,040 A | 11/1987 | Mueller et al. |
| 4,726,371 A | 2/1988 | Gibbens |
| 4,750,492 A | 6/1988 | Jacobs |
| 4,758,221 A | 7/1988 | Jureidini |
| 4,784,133 A | 11/1988 | Mackin |
| 4,798,594 A | 1/1989 | Hillstead |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,035,701 A | 7/1991 | Kabbara |
| 5,053,047 A | 10/1991 | Yoon |
| 5,064,431 A | 11/1991 | Gilbertson et al. |
| 5,078,731 A | 1/1992 | Hayhurst |
| 5,084,058 A | 1/1992 | Li |
| 5,087,263 A | 2/1992 | Li |
| 5,103,804 A | 4/1992 | Abele et al. |
| 5,108,368 A | 4/1992 | Hammerslag et al. |
| 5,133,723 A | 7/1992 | Li et al. |
| RE34,021 E | 8/1992 | Mueller et al. |
| 5,195,990 A | 3/1993 | Weldon |
| 5,203,337 A | 4/1993 | Feldman |
| 5,221,255 A | 6/1993 | Mahurkar et al. |
| 5,221,269 A | 6/1993 | Miller et al. |
| 5,234,448 A | 8/1993 | Wholey et al. |
| 5,242,456 A | 9/1993 | Nash et al. |
| 5,242,457 A | 9/1993 | Akopov et al. |
| 5,242,459 A | 9/1993 | Buelna |
| 5,257,975 A | 11/1993 | Foshee |
| 5,282,832 A | 2/1994 | Toso et al. |
| 5,306,296 A | 4/1994 | Wright et al. |
| 5,312,341 A | 5/1994 | Turi |
| 5,312,423 A | 5/1994 | Rosenbluth et al. |
| 5,314,407 A | 5/1994 | Auth et al. |
| 5,324,298 A | 6/1994 | Phillips et al. |
| 5,344,439 A | 9/1994 | Otten |
| 5,346,500 A | 9/1994 | Suchart |
| 5,350,133 A | 9/1994 | Morimoto |
| 5,358,479 A | 10/1994 | Wilson |
| 5,358,514 A | 10/1994 | Schulman et al. |
| 5,364,407 A | 11/1994 | Poll |
| 5,366,479 A | 11/1994 | McGarry et al. |
| 5,368,564 A | 11/1994 | Savage |
| 5,368,591 A | 11/1994 | Lennox et al. |
| 5,372,604 A | 12/1994 | Trott |
| 5,383,897 A | 1/1995 | Wholey |
| 5,383,905 A | 1/1995 | Golds et al. |
| 5,403,348 A | 4/1995 | Bonutti |
| 5,409,483 A | 4/1995 | Campbell et al. |
| 5,409,499 A | 4/1995 | Yi |
| 5,415,666 A | 5/1995 | Gourlay et al. |
| 5,417,700 A | 5/1995 | Egan |
| 5,423,837 A | 6/1995 | Mericle et al. |
| 5,431,659 A | 7/1995 | Ross, Jr. et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,507,725 A | 4/1996 | Savage et al. |
| 5,507,760 A | 4/1996 | Wynne et al. |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,531,686 A | 7/1996 | Lundquist et al. |
| 5,531,763 A | 7/1996 | Mastri et al. |
| 5,545,134 A | 8/1996 | Hilaire et al. |
| 5,545,168 A | 8/1996 | Burke |
| 5,565,122 A | 10/1996 | Zinnbauer et al. |
| 5,569,241 A | 10/1996 | Edwards |
| 5,571,215 A | 11/1996 | Sterman et al. |
| 5,584,835 A | 12/1996 | Greenfield |
| 5,591,194 A | 1/1997 | Berthiaume |
| 5,626,590 A | 5/1997 | Wilk |
| 5,626,614 A | 5/1997 | Hart |
| 5,630,824 A | 5/1997 | Hart |
| 5,632,755 A | 5/1997 | Nordgren et al. |
| 5,640,955 A | 6/1997 | Ockuly et al. |
| 5,643,289 A | 7/1997 | Sauer et al. |
| 5,665,109 A | 9/1997 | Yoon |
| 5,669,917 A | 9/1997 | Sauer et al. |
| 5,674,279 A | 10/1997 | Wright et al. |
| 5,690,655 A | 11/1997 | Hart et al. |
| 5,695,505 A | 12/1997 | Yoon |
| 5,702,397 A | 12/1997 | Goble et al. |
| 5,709,695 A | 1/1998 | Northrup, III |
| 5,713,950 A | 2/1998 | Cox |
| 5,716,370 A | 2/1998 | Williamson, IV et al. |
| 5,718,725 A | 2/1998 | Sterman et al. |
| 5,722,403 A | 3/1998 | McGee et al. |
| 5,725,542 A | 3/1998 | Yoon |
| 5,733,308 A | 3/1998 | Daugherty et al. |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,189 A | 6/1998 | Matsuno |
| 5,766,240 A | 6/1998 | Johnson |
| 5,769,812 A | 6/1998 | Stevens et al. |
| 5,779,673 A | 7/1998 | Roth et al. |
| 5,779,718 A | 7/1998 | Green et al. |
| 5,782,861 A | 7/1998 | Cragg et al. |
| 5,807,403 A | 9/1998 | Beyar et al. |
| 5,810,848 A | 9/1998 | Hayhurst |
| 5,810,853 A | 9/1998 | Yoon |
| 5,817,107 A | 10/1998 | Schaller |
| 5,824,066 A | 10/1998 | Gross |
| 5,827,171 A | 10/1998 | Dobak, III et al. |
| 5,843,169 A | 12/1998 | Taheri |
| 5,848,969 A | 12/1998 | Panescu et al. |
| 5,849,035 A | 12/1998 | Pathak et al. |
| 5,855,601 A | 1/1999 | Bessler et al. |
| 5,860,992 A | 1/1999 | Daniel et al. |
| 5,860,993 A | 1/1999 | Thompson et al. |
| 5,861,003 A | 1/1999 | Latson et al. |
| 5,868,733 A | 2/1999 | Ockuly et al. |
| 5,873,877 A | 2/1999 | McGaffigan et al. |
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A | 5/1999 | Swanson et al. |

(56) References Cited

U.S. PATENT DOCUMENTS

| | | |
|---|---|---|
| 5,904,657 A | 5/1999 | Unsworth et al. |
| 5,906,579 A | 5/1999 | Vander Salm et al. |
| 5,911,717 A | 6/1999 | Jacobsen et al. |
| 5,916,147 A | 6/1999 | Boury |
| 5,919,208 A | 7/1999 | Valenti |
| 5,935,149 A | 8/1999 | Ek |
| 5,940,651 A | 8/1999 | Pike et al. |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,984,933 A | 11/1999 | Yoon |
| 5,989,284 A | 11/1999 | Laufer |
| 5,991,650 A | 11/1999 | Swanson et al. |
| 6,010,531 A | 1/2000 | Donlon et al. |
| 6,013,083 A | 1/2000 | Bennett |
| 6,015,428 A | 1/2000 | Pagedas |
| 6,042,534 A | 3/2000 | Gellman et al. |
| 6,045,497 A | 4/2000 | Schweich, Jr. et al. |
| 6,050,936 A | 4/2000 | Schweich, Jr. et al. |
| 6,056,743 A | 5/2000 | Ellis et al. |
| 6,056,744 A | 5/2000 | Edwards |
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,080,182 A | 6/2000 | Shaw et al. |
| 6,086,608 A | 7/2000 | Ek et al. |
| 6,097,985 A | 8/2000 | Kasevich et al. |
| 6,099,553 A | 8/2000 | Hart et al. |
| 6,102,945 A | 8/2000 | Campbell |
| 6,110,184 A | 8/2000 | Weadock |
| 6,125,852 A | 10/2000 | Stevens et al. |
| 6,149,658 A | 11/2000 | Gardiner et al. |
| 6,152,934 A | 11/2000 | Harper et al. |
| 6,156,044 A | 12/2000 | Kammerer et al. |
| 6,162,168 A | 12/2000 | Schweich, Jr. et al. |
| 6,165,183 A | 12/2000 | Kuehn et al. |
| 6,171,317 B1 | 1/2001 | Jackson et al. |
| 6,171,329 B1 | 1/2001 | Shaw et al. |
| 6,183,469 B1 | 2/2001 | Thapliyal et al. |
| 6,193,714 B1 | 2/2001 | McGaffigan et al. |
| 6,197,017 B1 | 3/2001 | Brock et al. |
| 6,200,329 B1 | 3/2001 | Fung et al. |
| 6,203,531 B1 | 3/2001 | Ockuly et al. |
| 6,210,432 B1 | 4/2001 | Solem et al. |
| 6,221,084 B1 | 4/2001 | Fleenor |
| 6,228,055 B1 | 5/2001 | Foerster et al. |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,299,622 B1 | 10/2001 | Snow et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,461,327 B1 | 10/2002 | Addis et al. |
| 6,471,715 B1 | 10/2002 | Weiss |
| 6,491,689 B1 | 12/2002 | Ellis et al. |
| 6,506,190 B1 | 1/2003 | Walshe |
| 6,514,265 B2 | 2/2003 | Ho et al. |
| 6,524,328 B2 | 2/2003 | Levinson |
| 6,524,338 B1 | 2/2003 | Gundry |
| 6,533,753 B1 | 3/2003 | Haarstad et al. |
| 6,540,755 B2 | 4/2003 | Ockuly et al. |
| 6,551,332 B1 | 4/2003 | Nguyen et al. |
| 6,575,971 B2 | 6/2003 | Hauck et al. |
| 6,575,987 B2 | 6/2003 | Gellman et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,616,667 B1 | 9/2003 | Steiger et al. |
| 6,619,291 B2 | 9/2003 | Hlavka et al. |
| 6,626,899 B2 | 9/2003 | Houser et al. |
| 6,626,910 B1 | 9/2003 | Hugues |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,652,562 B2 | 11/2003 | Collier et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 6,723,107 B1 | 4/2004 | Skiba et al. |
| 6,733,509 B2 | 5/2004 | Nobles et al. |
| 6,746,457 B2 | 6/2004 | Dana et al. |
| 6,746,471 B2 | 6/2004 | Mortier et al. |
| 6,749,622 B2 | 6/2004 | McGuckin, Jr. et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,802,851 B2 | 10/2004 | Jones et al. |
| 6,811,560 B2 | 11/2004 | Jones et al. |
| 6,818,001 B2 | 11/2004 | Wulfman et al. |
| 6,849,077 B2 | 2/2005 | Ricci |
| 6,875,224 B2 | 4/2005 | Grimes |
| 6,908,424 B2 | 6/2005 | Mortier et al. |
| 6,913,608 B2 | 7/2005 | Liddicoat et al. |
| 6,923,818 B2 | 8/2005 | Muramatsu et al. |
| 6,932,792 B1 | 8/2005 | St. Goar et al. |
| 6,951,557 B2 | 10/2005 | Ellis et al. |
| 6,976,995 B2 | 12/2005 | Mathis et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,044,957 B2 | 5/2006 | Foerster et al. |
| 7,048,754 B2 | 5/2006 | Martin et al. |
| 7,094,246 B2 | 8/2006 | Anderson et al. |
| 7,101,395 B2 | 9/2006 | Tremulis et al. |
| 7,125,421 B2 | 10/2006 | Tremulis et al. |
| 7,160,312 B2 | 1/2007 | Saadat |
| 7,166,127 B2 | 1/2007 | Spence et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,214,230 B2 | 5/2007 | Brock et al. |
| 7,235,086 B2 | 6/2007 | Sauer et al. |
| 7,241,310 B2 | 7/2007 | Taylor et al. |
| 7,257,450 B2 | 8/2007 | Auth et al. |
| 7,326,231 B2 | 2/2008 | Phillips et al. |
| 7,331,972 B1 | 2/2008 | Cox |
| 7,335,213 B1 | 2/2008 | Hyde et al. |
| 7,344,544 B2 | 3/2008 | Bender et al. |
| 7,374,530 B2 | 5/2008 | Schaller |
| 7,381,210 B2 | 6/2008 | Zarbatany et al. |
| 7,390,329 B2 | 6/2008 | Westra et al. |
| 7,452,325 B2 | 11/2008 | Schaller |
| 7,534,204 B2 | 5/2009 | Starksen et al. |
| 7,588,582 B2 | 9/2009 | Starksen et al. |
| 7,618,449 B2 | 11/2009 | Tremulis et al. |
| 7,632,308 B2 | 12/2009 | Loulmet |

(56) References Cited

U.S. PATENT DOCUMENTS

| | | |
|---|---|---|
| 7,655,040 B2 | 2/2010 | Douk et al. |
| 7,666,193 B2 | 2/2010 | Starksen et al. |
| 7,699,892 B2 | 4/2010 | Rafiee et al. |
| 7,722,523 B2 | 5/2010 | Mortier et al. |
| 7,727,247 B2 | 6/2010 | Kimura et al. |
| 7,740,638 B2 | 6/2010 | Hyde |
| 7,753,858 B2 | 7/2010 | Starksen et al. |
| 7,753,922 B2 | 7/2010 | Starksen |
| 7,753,924 B2 | 7/2010 | Starksen et al. |
| 7,758,637 B2 | 7/2010 | Starksen et al. |
| 7,766,812 B2 | 8/2010 | Schroeder et al. |
| 7,776,812 B2 | 8/2010 | Lang et al. |
| 7,815,659 B2 | 10/2010 | Conlon et al. |
| 7,832,406 B2 | 11/2010 | Ellis et al. |
| 7,850,600 B1 | 12/2010 | Piskun |
| 7,883,538 B2 | 2/2011 | To et al. |
| 7,918,787 B2 | 4/2011 | Saadat |
| 7,922,762 B2 | 4/2011 | Starksen |
| 7,993,368 B2 | 8/2011 | Gambale et al. |
| 8,066,766 B2 | 11/2011 | To et al. |
| 8,287,555 B2 | 10/2012 | Starksen et al. |
| 8,287,557 B2 | 10/2012 | To et al. |
| 8,343,173 B2 | 1/2013 | Starksen et al. |
| 8,388,680 B2 | 3/2013 | Starksen et al. |
| 8,641,727 B2 | 2/2014 | Starksen et al. |
| 8,795,298 B2 | 8/2014 | Hernlund et al. |
| 9,072,513 B2 | 7/2015 | To et al. |
| 9,226,825 B2 | 1/2016 | Starksen et al. |
| 9,468,528 B2 | 10/2016 | Starksen et al. |
| 9,636,106 B2 | 5/2017 | Meier et al. |
| 9,706,996 B2 | 7/2017 | Nguyen et al. |
| 9,861,350 B2 | 1/2018 | Serina et al. |
| 9,949,829 B2 | 4/2018 | Starksen et al. |
| 10,092,402 B2 | 10/2018 | Starksen et al. |
| 10,363,392 B2 | 7/2019 | Legaspi et al. |
| 10,542,987 B2 | 1/2020 | Nguyen et al. |
| 10,624,741 B2 | 4/2020 | Starksen et al. |
| 10,625,046 B2 | 4/2020 | Fabro |
| 10,625,047 B2 | 4/2020 | Serina et al. |
| 10,667,914 B2 | 6/2020 | Sampson et al. |
| 10,898,328 B2 | 1/2021 | Starksen et al. |
| 10,980,973 B2 | 4/2021 | Nguyen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0034528 A1 | 10/2001 | Foerster et al. |
| 2001/0041821 A1 | 11/2001 | Wilk |
| 2001/0047165 A1 | 11/2001 | Makower et al. |
| 2002/0002401 A1 | 1/2002 | McGuckin, Jr. et al. |
| 2002/0007190 A1 | 1/2002 | Wulfman et al. |
| 2002/0013571 A1 | 1/2002 | Goldfarb et al. |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0035393 A1 | 3/2002 | Lashinski et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0077661 A1 | 6/2002 | Saadat |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0095180 A1 | 7/2002 | West, Jr. et al. |
| 2002/0099439 A1 | 7/2002 | Schwartz et al. |
| 2002/0116012 A1 | 8/2002 | May et al. |
| 2002/0133092 A1 | 9/2002 | Oslund et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0165561 A1 | 11/2002 | Ainsworth et al. |
| 2002/0173841 A1 | 11/2002 | Ortiz et al. |
| 2002/0183787 A1 | 12/2002 | Wahr et al. |
| 2002/0183835 A1 | 12/2002 | Taylor et al. |
| 2002/0193815 A1 | 12/2002 | Foerster et al. |
| 2002/0198536 A1 | 12/2002 | Trout, III et al. |
| 2003/0009196 A1 | 1/2003 | Peterson |
| 2003/0014060 A1 | 1/2003 | Wilson, Jr. et al. |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0045893 A1 | 3/2003 | Ginn |
| 2003/0060813 A1 | 3/2003 | Loeb et al. |
| 2003/0069577 A1 | 4/2003 | Vaska et al. |
| 2003/0069593 A1 | 4/2003 | Tremulis et al. |
| 2003/0074012 A1 | 4/2003 | Nguyen et al. |
| 2003/0074021 A1 | 4/2003 | Morriss et al. |
| 2003/0078465 A1 | 4/2003 | Pai et al. |
| 2003/0078601 A1 | 4/2003 | Shikhman et al. |
| 2003/0078603 A1 | 4/2003 | Schaller et al. |
| 2003/0093117 A1 | 5/2003 | Saadat |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144673 A1 | 7/2003 | Onuki et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0171776 A1 | 9/2003 | Adams et al. |
| 2003/0181800 A1 | 9/2003 | Bonutti |
| 2003/0181926 A1 | 9/2003 | Dana et al. |
| 2003/0191497 A1 | 10/2003 | Cope |
| 2003/0195562 A1 | 10/2003 | Collier et al. |
| 2003/0199974 A1 | 10/2003 | Lee et al. |
| 2003/0204205 A1 | 10/2003 | Sauer et al. |
| 2003/0220659 A1 | 11/2003 | Schmieding et al. |
| 2003/0220685 A1 | 11/2003 | Hlavka et al. |
| 2003/0225420 A1 | 12/2003 | Wardle |
| 2003/0229361 A1 | 12/2003 | Jackson |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0006358 A1 | 1/2004 | Wulfman et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0044365 A1 | 3/2004 | Bachman |
| 2004/0092962 A1 | 5/2004 | Thornton et al. |
| 2004/0093023 A1 | 5/2004 | Allen et al. |
| 2004/0093024 A1 | 5/2004 | Lousararian et al. |
| 2004/0093044 A1 | 5/2004 | Rychnovsky et al. |
| 2004/0097788 A1 | 5/2004 | Mourlas et al. |
| 2004/0097865 A1* | 5/2004 | Anderson .......... A61B 17/0467 604/22 |
| 2004/0118415 A1 | 6/2004 | Hall et al. |
| 2004/0122450 A1 | 6/2004 | Oren et al. |
| 2004/0133274 A1 | 7/2004 | Webler et al. |
| 2004/0148020 A1 | 7/2004 | Vidlund et al. |
| 2004/0152947 A1 | 8/2004 | Schroeder et al. |
| 2004/0162465 A1 | 8/2004 | Carrillo |
| 2004/0172046 A1 | 9/2004 | Hlavka et al. |
| 2004/0181238 A1 | 9/2004 | Zarbatany et al. |
| 2004/0186378 A1 | 9/2004 | Gesswein |
| 2004/0186486 A1 | 9/2004 | Roue et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0225300 A1 | 11/2004 | Goldfarb et al. |
| 2004/0236354 A1 | 11/2004 | Seguin |
| 2004/0236372 A1 | 11/2004 | Anspach, III et al. |
| 2004/0236419 A1 | 11/2004 | Milo |
| 2004/0243227 A1 | 12/2004 | Starksen et al. |

(56) References Cited

U.S. PATENT DOCUMENTS

| | | |
|---|---|---|
| 2004/0260317 A1 | 12/2004 | Bloom et al. |
| 2005/0021054 A1 | 1/2005 | Ainsworth et al. |
| 2005/0033325 A1 | 2/2005 | May et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0065589 A1 | 3/2005 | Schneider et al. |
| 2005/0075654 A1 | 4/2005 | Kelleher |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0137689 A1 | 6/2005 | Salahieh et al. |
| 2005/0143762 A1 | 6/2005 | Paraschac et al. |
| 2005/0165424 A1 | 7/2005 | Gallagher et al. |
| 2005/0177180 A1 | 8/2005 | Kaganov et al. |
| 2005/0184122 A1 | 8/2005 | Hlavka et al. |
| 2005/0192599 A1 | 9/2005 | Demarais |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0224884 A1 | 10/2005 | Sekigawa et al. |
| 2005/0228448 A1 | 10/2005 | Li |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267495 A1 | 12/2005 | Ginn et al. |
| 2005/0267571 A1 | 12/2005 | Spence et al. |
| 2005/0273128 A1 | 12/2005 | Reil |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0004409 A1 | 1/2006 | Nobis et al. |
| 2006/0009789 A1 | 1/2006 | Gambale et al. |
| 2006/0015144 A1 | 1/2006 | Burbank et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0106422 A1 | 5/2006 | Del Rio et al. |
| 2006/0122633 A1 | 6/2006 | To et al. |
| 2006/0129188 A1 | 6/2006 | Starksen et al. |
| 2006/0155363 A1 | 7/2006 | LaDuca et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0200199 A1 | 9/2006 | Bonutti et al. |
| 2006/0207606 A1 | 9/2006 | Roue et al. |
| 2006/0229697 A1 | 10/2006 | Gerdts et al. |
| 2006/0229708 A1 | 10/2006 | Powell et al. |
| 2006/0235413 A1 | 10/2006 | Denham et al. |
| 2006/0241340 A1 | 10/2006 | Schroeder et al. |
| 2006/0241656 A1 | 10/2006 | Starksen et al. |
| 2006/0241748 A1 | 10/2006 | Lee et al. |
| 2006/0264975 A1 | 11/2006 | Pipenhagen et al. |
| 2006/0265010 A1 | 11/2006 | Paraschac et al. |
| 2006/0270976 A1 | 11/2006 | Savage et al. |
| 2006/0271060 A1 | 11/2006 | Gordon |
| 2006/0271101 A1 | 11/2006 | Saadat et al. |
| 2006/0282161 A1 | 12/2006 | Huynh et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010852 A1 | 1/2007 | Blaeser et al. |
| 2007/0010857 A1 | 1/2007 | Sugimoto et al. |
| 2007/0016250 A1 | 1/2007 | Blaeser et al. |
| 2007/0016287 A1 | 1/2007 | Cartledge et al. |
| 2007/0032820 A1 | 2/2007 | Chin-Chen et al. |
| 2007/0038293 A1 | 2/2007 | St. Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0066994 A1 | 3/2007 | Blaeser et al. |
| 2007/0080188 A1 | 4/2007 | Spence et al. |
| 2007/0083259 A1 | 4/2007 | Bloom et al. |
| 2007/0093805 A1 | 4/2007 | Auth et al. |
| 2007/0100356 A1 | 5/2007 | Lucatero et al. |
| 2007/0106310 A1 | 5/2007 | Goldin et al. |
| 2007/0112244 A1 | 5/2007 | McCarthy et al. |
| 2007/0112422 A1 | 5/2007 | Dehdashtian |
| 2007/0112424 A1 | 5/2007 | Spence et al. |
| 2007/0112425 A1 | 5/2007 | Schaller et al. |
| 2007/0156172 A1 | 7/2007 | Alvarado |
| 2007/0213746 A1 | 9/2007 | Hahn et al. |
| 2007/0250161 A1 | 10/2007 | Dolan |
| 2007/0276437 A1 | 11/2007 | Call et al. |
| 2008/0004622 A1 | 1/2008 | Coe et al. |
| 2008/0033460 A1 | 2/2008 | Ziniti et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051703 A1 | 2/2008 | Thornton et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058765 A1 | 3/2008 | Jais et al. |
| 2008/0058868 A1 | 3/2008 | To et al. |
| 2008/0065156 A1 | 3/2008 | Hauser et al. |
| 2008/0097484 A1 | 4/2008 | Lim et al. |
| 2008/0097489 A1 | 4/2008 | Goldfarb et al. |
| 2008/0103439 A1 | 5/2008 | Torrance et al. |
| 2008/0119882 A1 | 5/2008 | Cox |
| 2008/0172035 A1 | 7/2008 | Starksen et al. |
| 2008/0177304 A1 | 7/2008 | Westra et al. |
| 2008/0177380 A1 | 7/2008 | Starksen et al. |
| 2008/0228032 A1 | 9/2008 | Starksen et al. |
| 2008/0228165 A1* | 9/2008 | Spence ............... A61B 17/0487 604/510 |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0294177 A1 | 11/2008 | To et al. |
| 2009/0012541 A1 | 1/2009 | Dahl et al. |
| 2009/0093670 A1 | 4/2009 | Annest et al. |
| 2009/0182417 A1 | 7/2009 | Tremulis et al. |
| 2009/0182418 A1 | 7/2009 | Solem et al. |
| 2009/0204125 A1 | 8/2009 | Onishi et al. |
| 2009/0209950 A1 | 8/2009 | Starksen |
| 2009/0222083 A1 | 9/2009 | Nguyen et al. |
| 2009/0234318 A1 | 9/2009 | Loulmet et al. |
| 2009/0264994 A1 | 10/2009 | Saadat |
| 2009/0276038 A1 | 11/2009 | Tremulis et al. |
| 2009/0292353 A1 | 11/2009 | Yoganathan et al. |
| 2010/0023056 A1 | 1/2010 | Johansson et al. |
| 2010/0023117 A1 | 1/2010 | Yoganathan et al. |
| 2010/0049213 A1 | 2/2010 | Serina et al. |
| 2010/0076408 A1 | 3/2010 | Krever et al. |
| 2010/0076548 A1 | 3/2010 | Konno |
| 2010/0082098 A1 | 4/2010 | Starksen et al. |
| 2010/0094213 A1 | 4/2010 | Horn et al. |

(56) References Cited

U.S. PATENT DOCUMENTS

| | | |
|---|---|---|
| 2010/0094314 A1 | 4/2010 | Hernlund et al. |
| 2010/0121349 A1 | 5/2010 | Meier et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2011/0098743 A1 | 4/2011 | Lyons et al. |
| 2011/0100173 A1* | 5/2011 | Stone ............... A61B 17/0482 83/13 |
| 2011/0160528 A1 | 6/2011 | Starksen |
| 2011/0207996 A1 | 8/2011 | Starksen |
| 2011/0276091 A1 | 11/2011 | Melanson et al. |
| 2012/0101442 A1 | 4/2012 | Legaspi et al. |
| 2012/0271331 A1 | 10/2012 | To et al. |
| 2013/0053870 A1* | 2/2013 | Evans ............... A61B 17/0467 606/144 |
| 2013/0190863 A1 | 7/2013 | Call et al. |
| 2013/0304093 A1 | 11/2013 | Serina et al. |
| 2014/0081252 A1 | 3/2014 | Bowe et al. |
| 2014/0135799 A1 | 5/2014 | Henderson |
| 2014/0142619 A1 | 5/2014 | Serina et al. |
| 2014/0148849 A1 | 5/2014 | Serina et al. |
| 2014/0155783 A1 | 6/2014 | Starksen et al. |
| 2014/0188140 A1 | 7/2014 | Meier et al. |
| 2014/0194976 A1 | 7/2014 | Starksen et al. |
| 2015/0164639 A1 | 6/2015 | Starksen et al. |
| 2015/0182216 A1 | 7/2015 | Morales et al. |
| 2015/0230919 A1 | 8/2015 | Chau et al. |
| 2016/0242765 A1* | 8/2016 | George ............... A61B 17/0467 |
| 2018/0140421 A1 | 5/2018 | Sampson et al. |
| 2019/0008505 A1 | 1/2019 | Sampson et al. |
| 2019/0091023 A1 | 3/2019 | Starksen et al. |
| 2019/0239872 A1 | 8/2019 | Serina et al. |
| 2020/0086082 A1 | 3/2020 | Legaspi et al. |
| 2020/0147343 A1 | 5/2020 | Fabro |
| 2020/0237516 A1 | 7/2020 | Sampson et al. |
| 2020/0345980 A1 | 11/2020 | Serina et al. |
| 2021/0220139 A1 | 7/2021 | Starksen et al. |

FOREIGN PATENT DOCUMENTS

| | | | |
|---|---|---|---|
| EP | 0669101 A1 | 8/1995 | |
| EP | 1919388 A2 | 5/2008 | |
| GB | 1370546 A | 10/1974 | |
| JP | H06237939 A | 8/1994 | |
| JP | H06510460 A | 11/1994 | |
| JP | H09289989 A | 11/1997 | |
| JP | H10506812 A | 7/1998 | |
| JP | H11506628 A | 6/1999 | |
| JP | H11318910 A | 11/1999 | |
| JP | 2000505336 A | 5/2000 | |
| JP | 2001500749 A | 1/2001 | |
| JP | 2003500121 A | 1/2003 | |
| JP | 2004000601 A | 1/2004 | |
| JP | 2004500170 A | 1/2004 | |
| JP | 2004321343 A | 11/2004 | |
| JP | 2005021576 A | 1/2005 | |
| JP | 2007514455 A | 6/2007 | |
| JP | 4823295 B2 | 11/2011 | |
| WO | WO-9308740 A1 | 5/1993 | |
| WO | WO-9403227 A1 | 2/1994 | |
| WO | WO-9515715 A1 | 6/1995 | |
| WO | WO-9608208 A1 | 3/1996 | |
| WO | WO-9610365 A1 | 4/1996 | |
| WO | WO-9639081 A1 | 12/1996 | |
| WO | WO-9639942 A1 | 12/1996 | |
| WO | WO-9727799 A1 | 8/1997 | |
| WO | WO-9727807 A1 | 8/1997 | |
| WO | WO-9729709 A1 | 8/1997 | |
| WO | WO-9730638 A1 | 8/1997 | |
| WO | WO-9730639 A1 | 8/1997 | |
| WO | WO-9807375 A1 | 2/1998 | |
| WO | WO-9846142 A1 | 10/1998 | |
| WO | WO-9959477 A1 | 11/1999 | |
| WO | WO-0060995 A2 | 10/2000 | |
| WO | WO-0067640 A2 | 11/2000 | |
| WO | WO-0071195 A1 | 11/2000 | |
| WO | WO-0119256 A1 | 3/2001 | |
| WO | WO-0060995 A3 | 4/2001 | |
| WO | WO-0067640 A3 | 4/2001 | |
| WO | WO-0126586 A1 | 4/2001 | |
| WO | WO-0137742 A2 | 5/2001 | |
| WO | WO-0154618 A1 | 8/2001 | |
| WO | WO-0200099 A2 | 1/2002 | |
| WO | WO-0203892 A1 | 1/2002 | |
| WO | WO-0234167 A2 | 5/2002 | |
| WO | WO-02051329 A1 | 7/2002 | |
| WO | WO-02053011 A2 | 7/2002 | |
| WO | WO-02074178 A2 | 9/2002 | |
| WO | WO-02085251 A1 | 10/2002 | |
| WO | WO-02085252 A1 | 10/2002 | |
| WO | WO-0234167 A3 | 2/2003 | |
| WO | WO-03049648 A2 | 6/2003 | |
| WO | WO-03053289 A1 | 7/2003 | |
| WO | WO-03073913 A2 | 9/2003 | |
| WO | WO-03075748 A2 | 9/2003 | |
| WO | WO-03088875 A1 | 10/2003 | |
| WO | WO-03097931 A1 | 11/2003 | |
| WO | WO-03105667 A2 | 12/2003 | |
| WO | WO-03105670 A2 | 12/2003 | |
| WO | WO-02053011 A3 | 2/2004 | |
| WO | WO-03105670 A3 | 3/2004 | |
| WO | WO-2004082538 A3 | 4/2004 | |
| WO | WO-2004037317 A2 | 5/2004 | |
| WO | WO-03105667 A3 | 6/2004 | |
| WO | WO-2004045367 A2 | 6/2004 | |
| WO | WO-2004037317 A3 | 8/2004 | |
| WO | WO-2004082523 A2 | 9/2004 | |
| WO | WO-2004082538 A2 | 9/2004 | |
| WO | WO-2004082523 A3 | 3/2005 | |
| WO | WO-2005025644 A2 | 3/2005 | |
| WO | WO-2005062931 A2 | 7/2005 | |
| WO | WO-2005062931 A3 | 10/2005 | |
| WO | WO-2005102181 A1 | 11/2005 | |
| WO | WO-2005110241 A1 | 11/2005 | |
| WO | WO-2006034243 A2 | 3/2006 | |
| WO | WO-2006037073 A2 | 4/2006 | |
| WO | WO-2006039296 A2 | 4/2006 | |
| WO | WO-2006097931 A2 | 9/2006 | |
| WO | WO-2006116558 A2 | 11/2006 | |
| WO | WO-2006128092 A2 | 11/2006 | |
| WO | WO-2007001936 A2 | 1/2007 | |
| WO | WO-2007005495 A1 | 1/2007 | |
| WO | WO-2007021564 A1 | 2/2007 | |
| WO | WO-2007021597 A2 | 2/2007 | |
| WO | WO-2007021834 A1 | 2/2007 | |
| WO | WO-2007035449 A2 | 3/2007 | |
| WO | WO-2005025644 A3 | 5/2007 | |
| WO | WO-2007056502 A1 | 5/2007 | |
| WO | WO-2006097931 A3 | 7/2007 | |
| WO | WO-2007095052 A2 | 8/2007 | |
| WO | WO-2006116558 A3 | 9/2007 | |
| WO | WO-2007100409 A2 | 9/2007 | |
| WO | WO-2008028135 A2 | 3/2008 | |
| WO | WO-2008042987 A2 | 4/2008 | |
| WO | WO-2008048626 A2 | 4/2008 | |
| WO | WO-2008088716 A1 | 7/2008 | |
| WO | WO-2008028135 A3 | 8/2008 | |
| WO | WO-2008108936 A1 | 9/2008 | |
| WO | WO-2008112740 A2 | 9/2008 | |
| WO | WO-2009052427 A1 | 4/2009 | |
| WO | WO-2009052438 A2 | 4/2009 | |
| WO | WO-2009052509 A1 | 4/2009 | |
| WO | WO-2007021597 A3 | 5/2009 | |
| WO | WO-2009061611 A1 | 5/2009 | |
| WO | WO-2009100242 A1 | 8/2009 | |
| WO | WO-2009105720 A2 | 8/2009 | |
| WO | WO-2009137712 A1 | 11/2009 | |
| WO | WO-2010011698 A1 | 1/2010 | |
| WO | WO-2010042845 A1 | 4/2010 | |
| WO | WO-2010042857 A1 | 4/2010 | |
| WO | WO-2010051029 A1 | 5/2010 | |
| WO | WO-2010085456 A1 | 7/2010 | |

(56) References Cited

FOREIGN PATENT DOCUMENTS

| WO | WO-2010085457 A1 | 7/2010 |
|---|---|---|
| WO | WO-2010120812 A1 | 10/2010 |
| WO | WO-2012031204 A2 | 3/2012 |
| WO | WO-2012036798 A1 | 3/2012 |
| WO | WO-2012031204 A3 | 4/2012 |
| WO | WO-2012112967 A1 | 8/2012 |
| WO | WO-2012161769 A1 | 11/2012 |
| WO | WO-2016141358 A1 | 9/2016 |
| WO | WO-2016183386 A1 | 11/2016 |
| WO | WO-2018094258 A1 | 5/2018 |
| WO | WO-2021011659 A1 | 1/2021 |

OTHER PUBLICATIONS

Co-pending U.S. Appl. No. 10/901,444, inventors Starksen; Niel F. et al., filed Jul. 27, 2004.
Co-pending U.S. Appl. No. 10/901,455, inventors Starksen; Niel F. et al., filed Jul. 27, 2004.
Co-pending U.S. Appl. No. 10/901,555, inventors Starksen; Niel F. et al., filed Jul. 27, 2004.
Co-pending U.S. Appl. No. 11/137,833, inventors Starksen; Niel F. et al., filed May 24, 2005.
Co-pending U.S. Appl. No. 11/201,949, inventors To; John et al., filed Aug. 10, 2005.
Co-pending U.S. Appl. No. 11/202,474, inventors To; John et al., filed Aug. 11, 2005.
Co-pending U.S. Appl. No. 11/232,190, inventors To; John et al., filed Sep. 20, 2005.
Co-pending U.S. Appl. No. 11/237,461, inventors Starksen; Niel F. et al., filed Sep. 27, 2005.
Co-pending U.S. Appl. No. 11/255,400, inventors Starksen; Niel F. et al., filed Oct. 20, 2005.
Co-pending U.S. Appl. No. 11/270,034, inventors To; John et al., filed Nov. 8, 2005.
Co-pending U.S. Appl. No. 11/414,657, inventors Starksen; Niel F. et al., filed Apr. 27, 2006.
Corbion Purac (2015). PURASORB Polymers: Products for Medical Devices, 2 total pages.
Corbion Purac (2015). Technology Summary, 1 total page.
Corrected Notice of Allowance dated Apr. 3, 2020 for U.S. Appl. No. 15/817,015, filed Nov. 17, 2017, 2 pages.
De Simone, R. et al. (Apr. 1, 1994). "Adjustable Annuloplasty for Tricuspid Insufficiency with External Control," Reader's Comments and Reply, Am. J. Cardiol. 73(9):721-722.
De Simone, R. et al. (Apr. 15, 1993). "Adjustable Tricuspid Valve Annuloplasty Assisted by Intraoperative Transesophageal Color Doppler Echocardiography," Am. J. Cardiol. 71(11):926-931.
De Simone, R. et al. (Apr. 15, 1993). "Adjustable Tricuspid Valve Annuloplasty Assisted by Intraoperative Transesophageal Color Doppler Echocardiography," Am. J. Cardiol. 73:721-722. (As cited in IDS in parents—actually combined two articles listed above.).
Downing, S.W. et al. (2002). "Feasibility of Off-Pump ASD Closure Using Real-Time 3-D Echocardiography," The Heart Surgery Forum 5(2):96-99, Abstract 7025.
European Examination Communication dated Dec. 8, 2009, for EP Application No. 06 837 222.6 filed on Nov. 8, 2006, 3 pages.
European Search Report dated Dec. 6, 2011, for EP Patent Application No. 11187159.6, filed on Oct. 16, 2007, 5 pages.
Extended European Search Report dated Jul. 31, 2020 for EP Application No. 17871289.9. 9 pages.
Extended European Search Report dated Dec. 12, 2018, for EP Patent Application No. 18170269.7, filed on Sep. 1, 2004, 7 Pages.
Extended European Search Report dated Dec. 3, 2018 for EP Patent Application No. 18167829.3, filed on Oct. 16, 2007, 8 pages.
Extended European Search Report dated Jun. 2, 2010 for EP Patent Application No. 07852809.8, filed on Oct. 16, 2007, 8 pages. (28.43).
Extended European Search Report dated May 17, 2016, for EP Application No. 09 819 970.6, filed on May 4, 2011, 8 pages.—(37.xx).
Extended European Search Report dated Sep. 16, 2011, for EP Patent Application No. 11158898.4, filed on Sep. 1, 2004, 8 pages. (15.72).
Extended European Search Report dated Sep. 9, 2011, for EP Patent Application No. 11158896.8, filed on Sep. 1, 2004, 7 pages. (15.73).
Final Office Action dated Feb. 24, 2016, for U.S. Appl. No. 13/948,009, filed Jul. 22, 2013. 13 pages. (31.10).
Final Office Action dated Feb. 5, 2015, for U.S. Appl. No. 13/540,499, filed Jul. 2, 2012, 10 pages. (25015.05).
Final Office Action dated May 18, 2015, for U.S. Appl. No. 10/901,554, filed Jul. 27, 2004, 17 pages. (15.23).
Final Office Action dated Apr. 10, 2009, for U.S. Appl. No. 11/255,400, filed Oct. 20, 2005, 8 pages. (15.27).
Final Office Action dated Apr. 10, 2009, for U.S. Appl. No. 11/414,657, filed Apr. 27, 2006, 8 pages. (15.03).
Final Office Action dated Apr. 14, 2008, for U.S. Appl. No. 10/901,019, filed Jul. 27, 2004, 11 pages. (15.01).
Final Office Action dated Apr. 15, 2010, for U.S. Appl. No. 11/201,949, filed Aug. 10, 2005, 8 pages. (25.00).
Final Office Action dated Apr. 2, 2008, for U.S. Appl. No. 10/792,681, filed Mar. 2, 2004, 15 pages.
Final Office Action dated Apr. 20, 2011, for U.S. Appl. No. 11/414,657, filed Apr. 27, 2006, 8 pages. (15.03).
Final Office Action dated Apr. 27, 2009, for U.S. Appl. No. 10/901,455, filed Jul. 27, 2004, 11 pages. (17.00).
Final Office Action dated Apr. 29, 2009, for U.S. Appl. No. 10/901,019, filed Jul. 27, 2004, 9 pages. (15.01).
Final Office Action dated Aug. 1, 2008, for U.S. Appl. No. 11/232,190, filed Sep. 20, 2005, 8 pages. (15.26).
Final Office Action dated Aug. 13, 2007, for U.S. Appl. No. 10/900,980, filed Jul. 27, 2004, 9 pages. (15.24).
Final Office Action dated Aug. 14, 2007, for U.S. Appl. No. 11/255,400, filed Oct. 20, 2005, 8 pages. (15.27).
Final Office Action dated Aug. 19, 2008, for U.S. Appl. No. 10/901,444, filed Jul. 27, 2004, 9 pages.
Final Office Action dated Aug. 24, 2017, for U.S. Appl. No. 13/948,009, filed Jul. 22, 2013, 19 pages.
Final Office Action dated Aug. 30, 2007, for U.S. Appl. No. 11/232,190, filed Sep. 20, 2005, 9 pages. (15.26).
Final Office Action dated Aug. 4, 2011, for U.S. Appl. No. 10/900,980, filed Jul. 27, 2004, 9 pages. (15.24).
Final Office Action dated Aug. 5, 2014, for U.S. Appl. No. 10/776,682, filed Feb. 10, 2004, 7 pages. (5.10).
Final Office Action dated Aug. 6, 2007, for U.S. Appl. No. 10/901,019, filed Jul. 27, 2004, 12 pages. (15.01).
Final Office Action dated Aug. 6, 2007, for U.S. Appl. No. 11/137,833, filed May 24, 2005, 8 pages. (15.02).
Final Office Action dated Dec. 26, 2007, for U.S. Appl. No. 10/776,682, filed Feb. 10, 2004, 6 pages. (5.10) (.47 series chart).
Final Office Action dated Dec. 26, 2014, for U.S. Appl. No. 13/820,447, filed Sep. 2, 2011, 8 pages.—(53.00).
Final Office Action dated Dec. 6, 2011, for U.S. Appl. No. 12/366,553, filed Feb. 5, 2009, 7 pages. (34.00).
Final Office Action dated Feb. 24, 2011, for U.S. Appl. No. 11/894,397, filed Aug. 20, 2007, 12 pages. (15.06).
Final Office Action dated Feb. 24, 2011, for U.S. Appl. No. 11/894,468, filed Aug. 20, 2007, 12 pages. (15.08).
Final Office Action dated Feb. 4, 2016, for U.S. Appl. No. 14/626,826, filed Feb. 19, 2015, 9 pages. (25015.07).
Final Office Action dated Feb. 6, 2007, for U.S. Appl. No. 10/656,797, filed Sep. 4, 2003, 8 pages. (15.00).
Final Office Action dated Jan. 12, 2009, for U.S. Appl. No. 10/776,682, filed Feb. 10, 2004, 8 pages. (5.10).
Final Office Action dated Jan. 17, 2012, for U.S. Appl. No. 11/656,141, filed Jan. 19, 2007, 12 pages. (1.00) cite in 15.03 only.
Final Office Action dated Jan. 22, 2008, for U.S. Appl. No. 10/927,784, filed Aug. 27, 2004, 10 pages. (12.00).
Final Office Action dated Jan. 22, 2009, for U.S. Appl. No. 11/255,400, filed Oct. 20, 2005, 9 pages. (15.27).

(56) References Cited

OTHER PUBLICATIONS

Final Office Action dated Jan. 22, 2013, for U.S. Appl. No. 12/480,568, filed Jun. 8, 2009, 6 pages. (31.01).
Final Office Action dated Jan. 24, 2014, for U.S. Appl. No. 11/201,949, filed Aug. 10, 2005, 10 pages. (25.00).
Final Office Action dated Jul. 11, 2011, for U.S. Appl. No. 12/133,319, filed Jun. 4, 2008, 8 pages. (16.02).
Final Office Action dated Jul. 12, 2007, for U.S. Appl. No. 11/202,474, filed Aug. 11, 2005, 10 pages. (15.25).
Final Office Action dated Jul. 21, 2009, for U.S. Appl. No. 11/270,034, filed Nov. 8, 2005, 8 pages. (15.28).
Final Office Action dated Jul. 24, 2007, for U.S. Appl. No. 10/741,130, filed Dec. 19, 2003, 10 pages. (15.20).
Final Office Action dated Jul. 26, 2010, for U.S. Appl. No. 11/270,034, filed Nov. 8, 2005, 8 pages. (15.28).
Final Office Action dated Jul. 29, 2019, for U.S. Appl. No. 15/474,877, filed Mar. 30, 2017, 8 pages.
Final Office Action dated Jul. 7, 2016, for U.S. Appl. No. 14/033,369, filed Sep. 20, 2013, 9 pages. (37.01).
Final Office Action dated Jun. 11, 2012, for U.S. Appl. No. 12/187,331, filed Aug. 6, 2008, 7 pages. (25015.03).
Final Office Action dated Jun. 11, 2012, for U.S. Appl. No. 12/132,161, filed Jun. 3, 2008, 13 pages. (15.11).
Final Office Action dated Jun. 4, 2008, for U.S. Appl. No. 11/202,474, filed Aug. 11, 2005, 10 pages. (15.25).
Final Office Action dated Jun. 6, 2011, for U.S. Appl. No. 11/201,949, filed Aug. 10, 2005, 10 pages. (25.00).
Final Office Action dated Jun. 8, 2010, for U.S. Appl. No. 10/792,681, filed Mar. 2, 2004, 17 pages. (15.21).
Final Office Action dated Mar. 11, 2009, for U.S. Appl. No. 10/656,797, filed Sep. 4, 2003, 10 pages. (15.00).
Final Office Action dated Mar. 17, 2011, for U.S. Appl. No. 10/901,554, filed Jul. 27, 2004, 13 pages. (15.23).
Final Office Action dated Mar. 17, 2011, for U.S. Appl. No. 11/202,474, filed Aug. 11, 2005, 9 pages. (15.25).
Final Office Action dated Mar. 19, 2012, for U.S. Appl. No. 12/574,563, filed Oct. 6, 2009, 6 pages. (34.01).
Final Office Action dated Mar. 20, 2013, for U.S. Appl. No. 12/577,044, filed Oct. 9, 2009, 7 pages. (37.00).
Final Office Action dated Mar. 25, 2010, for U.S. Appl. No. 10/900,980, filed Jul. 27, 2004, 8 pages. (15.24).
Final Office Action dated Mar. 3, 2010, for U.S. Appl. No. 11/414,657, filed Apr. 27, 2006, 7 pages. (15.03).
Final Office Action dated May 11, 2010, for U.S. Appl. No. 11/237,461, filed Sep. 27, 2005, 6 pages. (5.01).
Final Office Action dated May 12, 2010, for U.S. Appl. No. 11/583,627, filed Oct. 18, 2006, 18 pages. (28.00).
Final Office Action dated May 15, 2015, for U.S. Appl. No. 13/820,447, filed Oct. 18, 2013, 11 pages. (53.00).
Final Office Action dated May 19, 2016, for U.S. Appl. No. 13/820,447, filed Oct. 18, 2013, 10 pages. (53.00).
Final Office Action dated May 28, 2008, for U.S. Appl. No. 11/270,034, filed Nov. 8, 2005, 10 pages. (15.28).
Final Office Action dated May 8, 2009, for U.S. Appl. No. 11/201,949, filed Aug. 10, 2005, 10 pages. (25.00).
Final Office Action dated Nov. 10, 2009, for U.S. Appl. No. 10/741,130, filed Dec. 19, 2003, 9 pages. (15.20).
Final Office Action dated Nov. 10, 2011, for U.S. Appl. No. 10/792,681, filed Mar. 2, 2004, 20 pages. (15.21).
Final Office Action dated Nov. 22, 2010, for U.S. Appl. No. 11/237,461, filed Sep. 27, 2005, 5 pages. (5.01).
Final Office Action dated Nov. 26, 2010, for U.S. Appl. No. 11/894,340, filed Aug. 20, 2007, 12 pages. (15.04).
Final Office Action dated Nov. 28, 2011, for U.S. Appl. No. 11/201,949, filed Aug. 10, 2005, 8 pages. (25.00).
Final Office Action dated Nov. 29, 2010, for U.S. Appl. No. 11/894,463, filed Aug. 20, 2007, 12 pages. (15.07).
Final Office Action dated Nov. 3, 2011, for U.S. Appl. No. 12/581,040, filed Oct. 16, 2009, 5 pages. (15.12).
Final Office Action dated Nov. 3, 2017, for U.S. Appl. No. 13/540,499, filed Jul. 2, 2012, 10 pages.
Final Office Action dated Oct. 13, 2009, for U.S. Appl. No. 10/901,554, filed Jul. 27, 2004, 11 pages. (15.23).
Final Office Action dated Oct. 14, 2008, for U.S. Appl. No. 10/741,130, filed Dec. 19, 2003, 9 pages. (15.20).
Final Office Action dated Oct. 19, 2009, for U.S. Appl. No. 10/901,444, filed Jul. 27, 2004, 9 pages. (16.00).
Final Office Action dated Oct. 22, 2010, for U.S. Appl. No. 10/776,682, filed Feb. 10, 2004, 10 pages. (5.10).
Final Office Action dated Oct. 23, 2012, for U.S. Appl. No. 12/576,955, filed Oct. 9, 2009, 8 pages. (20040.00).
Final Office Action dated Oct. 30, 2007, for U.S. Appl. No. 10/656,797, filed Sep. 4, 2003, 6 pages. (15.00).
Final Office Action dated Oct. 6, 2010, for U.S. Appl. No. 12/132,375, filed Jun. 3, 2008, 9 pages. (15.10).
Final Office Action dated Sep. 11, 2007, for U.S. Appl. No. 10/901,444, filed Jul. 27, 2004, 10 pages. (16.00).
Final Office Action dated Sep. 14, 2007, for U.S. Appl. No. 10/927,784, filed Aug. 27, 2004, 13 pages. (12.00).
Final Office Action dated Sep. 14, 2017, for U.S. Appl. No. 14/626,826, filed Feb. 19, 2015, 8 pages.
Final Office Action dated Sep. 15, 2010, for U.S. Appl. No. 11/894,401, filed Aug. 20, 2007, 6 pages. (25015.01).
Final Office Action dated Sep. 2, 2009, for U.S. Appl. No. 11/232,190, filed Sep. 20, 2005, 8 pages. (15.26).
Final Office Action dated Sep. 27, 2010, for U.S. Appl. No. 11/656,141, filed Jan. 19, 2007, 10 pages. (1.00) cite in 15.03 only.
Final Office Action dated Sep. 28, 2009, for U.S. Appl. No. 11/202,474, filed Aug. 11, 2005, 10 pages. (15.25).
Final Office Action dated Sep. 30, 2008, for U.S. Appl. No. 10/900,980, filed Jul. 27, 2004, 7 pages. (15.24).
International Preliminary Report on Patentability dated Apr. 30, 2008, for PCT Application PCT/US2007/022122 filed on Oct. 16, 2007, 9 pages.—(28.40).
International Preliminary Report on Patentability dated Jul. 21, 2009, for PCT Application No. PCT/US2008/000351, filed on Jan. 9, 2008, 7 pages.
International Preliminary Report on Patentability dated Jul. 30, 2009, for PCT Application No. PCT/US2008/000351, filed on Jan. 9, 2008, 8 pages. (1.40) cite in 15.03 only.
International Search Report and Written Opinion for Application No. PCT/US2020/042145, dated Oct. 1, 2020, 15 pages.
International Search Report and Written Opinion dated Mar. 8, 2018, for PCT Patent Application No. PCT/US2017/062382, filed on Nov. 17, 2017, 15 pages.
International Search Report dated Dec. 19, 2006, for PCT Application No. PCT/US2006/031190, filed Aug. 10, 2006, 3 pages. (15.46).
International Search Report dated Apr. 2, 2007, for PCT Application No. PCT/US2006/043597, filed Nov. 8, 2006, 4 pages. (15.48).
International Search Report dated Dec. 10, 2009, for PCT Patent Application No. PCT/US2009/060202, filed on Oct. 9, 2009, 3 pages. (37.40).
International Search Report dated Feb. 21, 2012, for PCT Patent Application No. PCT/US2011/050331, filed on Sep. 2, 2011, 4 pages.—(53.40).
International Search Report dated Feb. 3, 2004, for PCT Application No. PCT/US2003/018874, filed on Jun. 13, 2003, 3 pages.
International Search Report dated Jan. 12, 2010, for PCT Patent Application No. PCT/US09/60227, filed on Oct. 9, 2009, 2 pages. (40.40).
International Search Report dated Mar. 19, 2010, for PCT Patent Application No. PCT/US2010/021437, filed on Jan. 19, 2010, 2 pages. (47.40).
International Search Report dated Mar. 7, 2007, for PCT Patent Application No. PCT/US2004/028431, filed on Sep. 1, 2004, 1 page.—(15.40).
International Search Report dated Mar. 8, 2018, for PCT Patent Application No. PCT/US2017/062382, filed on Nov. 17, 2017, 4 pages.

(56) References Cited

OTHER PUBLICATIONS

International Search Report dated Mar. 9, 2010, for PCT Patent Application No. PCT/US/2010/021440, filed on Jan. 19, 2010, 1 page. (42.40).
International Search Report dated May 19, 2009, for PCT Patent Application No. PCT/US2008/080381, filed on Oct. 17, 2008, 5 pages. (31.40).
International Search Report dated May 21, 2008, for PCT Application No. PCT/US2008/000351, filed on Jan. 9, 2008, 2 pages. (1.40) cite in 15.03 only.
International Search Report dated May 6, 2008 for PCT Application PCT/US07/22122 filed on Oct. 16, 2007, 1 page. (28.40).
Nagy, Z.L. et al. (Dec. 2000). "Mitral Annuloplasty with a Suture Technique," European Journal of Cardio-thoracic Surgery 18(6):739-740.
Non-Final Office Action dated Aug. 26, 2009, for U.S. Appl. No. 11/414,657, filed Apr. 27, 2006, 6 pages. (15.03).
Non-Final Office Action dated Aug. 30, 2007, for U.S. Appl. No. 11/270,034 filed Nov. 8, 2005, 10 pages. (15.28) (28 series chart).
Non-Final Office Action dated Jan. 9, 2008, for U.S. Appl. No. 11/232,190, filed Sep. 20, 2005, 8 pages. (15.26).
Non-Final Office Action dated Jun. 18, 2015, for U.S. Appl. No. 13/948,009, filed Jul. 22, 2013, 20 pages.
Non-Final Office Action dated Nov. 17, 2016, for U.S. Appl. No. 13/948,009, filed Jul. 22, 2013, 22 pages.
Non-Final Office Action dated Oct. 3, 2014, for U.S. Appl. No. 14/033,369, filed Sep. 20, 2013, 6 pages. (37.01).
Non-Final Office Action dated Apr. 11, 2013, for U.S. Appl. No. 12/657,422, filed Jan. 19, 2010, 8 pages. (25.00).
Non-Final Office Action dated Apr. 14, 2010, for U.S. Appl. No. 11/656,141, filed Jan. 19, 2007, 10 pages. (1.00) cite in 15.03 only.
Non-Final Office Action dated Apr. 15, 2010, for U.S. Appl. No. 10/776,682, filed Feb. 10, 2004, 9 pages. (5.10).
Non-Final Office Action dated Apr. 2, 2010, for U.S. Appl. No. 12/132,375, filed Jun. 3, 2008, 9 pages. (15.10).
Non-Final Office Action dated Apr. 21, 2016, for U.S. Appl. No. 13/540,499, filed Jul. 2, 2012, 12 pages. (25015.05).
Non-Final Office Action dated Apr. 27, 2011, for U.S. Appl. No. 12/366,533, filed Feb. 5, 2009, 9 pages. (34.00).
Non-Final Office Action dated Apr. 29, 2008, for U.S. Appl. No. 10/901,455, filed Jul. 27, 2004, 9 pages. (17.00).
Non-Final Office Action dated Apr. 30, 2009, for U.S. Appl. No. 10/901,444, filed Jul. 27, 2004, 9 pages. (16.00).
Non-Final Office Action dated Apr. 8, 2013, for U.S. Appl. No. 11/414,657, filed Apr. 27, 2006, 9 pages. (15.03).
Non-Final Office Action dated Aug. 1, 2007, for U.S. Appl. No. 10/792,681, filed Mar. 2, 2004, 16 pages. (15.21).
Non-Final Office Action dated Aug. 17, 2010, for U.S. Appl. No. 11/414,657, filed Apr. 27, 2006, 7 pages. (15.03).
Non-Final Office Action dated Aug. 19, 2009, for U.S. Appl. No. 11/583,627, filed Oct. 18, 2006, 14 pages. (28.00).
Non-Final Office Action dated Aug. 20, 2010, for U.S. Appl. No. 10/901,554, filed Jul. 27, 2004, 13 pages. (15.23).
Non-Final Office Action dated Aug. 22, 2006, for U.S. Appl. No. 10/656,797, filed Sep. 4, 2003, 6 pages. (15.00).
Non-Final Office Action dated Aug. 25, 2009, for U.S. Appl. No. 10/900,980, filed Jul. 27, 2004, 7 pages. (15.24).
Non-Final Office Action dated Aug. 29, 2008, for U.S. Appl. No. 10/792,681, filed Mar. 2, 2004, 15 pages. (15.21).
Non-Final Office Action dated Aug. 6, 2008, for U.S. Appl. No. 10/776,682, filed Feb. 10, 2004, 7 pages. (5.10).
Non-Final Office Action dated Aug. 9, 2006, for U.S. Appl. No. 10/900,980, filed Jul. 27, 2004, 17 pages. (15.24).
Non-Final Office Action dated Dec. 16, 2010, for U.S. Appl. No. 12/133,319, filed Jun. 4, 2008, 10 pages.
Non-Final Office Action dated Dec. 18, 2015, for U.S. Appl. No. 14/033,369, filed Sep. 20, 2013, 7 pages. (37.01).
Non-Final Office Action dated Dec. 21, 2010, for U.S. Appl. No. 12/133,306, filed Jun. 4, 2008, 13 pages. (16.01).
Non-Final Office Action dated Dec. 22, 2011, for U.S. Appl. No. 11/270,034, filed Nov. 8, 2005, 8 pages. (15.28).
Non-Final Office Action dated Dec. 27, 2006, for U.S. Appl. No. 10/741,130, filed Dec. 19, 2003, 9 pages. (15.20).
Non-Final Office Action dated Dec. 27, 2006, for U.S. Appl. No. 11/270,034 filed Nov. 8, 2005, 8 pages. (15.28).
Non-Final Office Action dated Feb. 11, 2011, for U.S. Appl. No. 12/132,328, filed Jun. 3, 2008, 9 pages. (5.02).
Non-Final Office Action dated Feb. 17, 2012, for U.S. Appl. No. 12/133,319, filed Jun. 4, 2008, 7 pages.(16.02).
Non-Final Office Action dated Feb. 17, 2017, for U.S. Appl. No. 14/626,826, filed Feb. 19, 2015, 11 pages.
Non-Final Office Action dated Feb. 17, 2017, for U.S. Appl. No. 13/820,447, filed Oct. 18, 2013, 11 pages.
Non-Final Office Action dated Feb. 18, 2010, for U.S. Appl. No. 11/894,401, filed Aug. 20, 2007, 6 pages. (25015.01) 5.02 ONLY.
Non-Final Office Action dated Feb. 2, 2011, for U.S. Appl. No. 12/581,040, filed Oct. 16, 2009, 5 pages. (15.12).
Non-Final Office Action dated Feb. 27, 2007, for U.S. Appl. No. 11/202,474, filed Aug. 11, 2005, 8 pages. (15.25).
Non-Final Office Action dated Jan. 13, 2009, for U.S. Appl. No. 10/901,555, filed Jul. 27, 2004, 11 pages. (15.22).
Non-Final Office Action dated Jan. 16, 2008, for U.S. Appl. No. 10/901,444, filed Jul. 27, 2004, 9 pages. (16.00).
Non-Final Office Action dated Jan. 17, 2007, for U.S. Appl. No. 10/901,444, filed Jul. 27, 2004, 11 pages. (16.00).
Non-Final Office Action dated Jan. 19, 2010, for U.S. Appl. No. 11/270,034, filed Nov. 8, 2005, 10 pages. (15.28).
Non-Final Office Action dated Jan. 23, 2009, for U.S. Appl. No. 11/232,190, filed Sep. 20, 2005, 8 pages. (15.26).
Non-Final Office Action dated Jan. 23, 2009, for U.S. Appl. No. 11/270,034, filed Nov. 8, 2005, 8 pages. (15.28).
Non-Final Office Action dated Jan. 26, 2017, for U.S. Appl. No. 13/540,499, filed Jul. 2, 2012, 10 pages.
Non-Final Office Action dated Jan. 27, 2012, for U.S. Appl. No. 12/480,568, filed Jun. 8, 2009, 5 pages. (31.01) Termination Only.
Non-Final Office Action datedJan. 29, 2009, for U.S. Appl. No. 10/900,980, filed Jul. 27, 2004, 6 pages. (15.24).
Non-Final Office Action dated Jan. 31, 2008, for U.S. Appl. No. 11/255,400, filed Oct. 20, 2005, 7 pages. (15.27).
Non-Final Office Action dated Jan. 4, 2007, for U.S. Appl. No. 11/255,400, filed Oct. 20, 2005, 7 pages. (15.27).
Non-Final Office Action dated Jul. 24, 2007, for U.S. Appl. No. 10/656,797, filed Sep. 4, 2003, 6 pages. (15.00).
Non-Final Office Action dated Jul. 29, 2011, for U.S. Appl. No. 12/574,563, filed Oct. 6, 2009, 5 pages. (34.01).
Non-Final Office Action dated Jul. 6, 2009, for U.S. Appl. No. 10/776,682, filed Feb. 10, 2004, 9 pages. (5.10).
Non-Final Office Action dated Jun. 12, 2008, for U.S. Appl. No. 10/927,784, filed Aug. 27, 2004, 11 pages. (12.00).
Non-Final Office Action dated Jun. 12, 2018, for U.S. Appl. No. 13/948,009, filed Jul. 22, 2013, 22 pages.
Non-Final Office Action dated Jun. 16, 2016, for U.S. Appl. No. 14/589,855, filed Jan. 5, 2015, 9 pages. (5.03).
Non-Final Office Action dated Jun. 21, 2010, for U.S. Appl. No. 11/894,397, filed Aug. 20, 2007, 13 pages.
Non-Final Office Action dated Jun. 21, 2013, for U.S. Appl. No. 11/201,949, filed Aug. 10, 2005, 8 pages.
Non-Final Office Action dated Jun. 28, 2012, for U.S. Appl. No. 12/577,044, filed Oct. 9, 2009, 7 pages. (37.00).
Non-Final Office Action dated Jun. 6, 2008, for U.S. Appl. No. 10/656,797, filed Sep. 4, 2003, 5 pages. (15.00).
Non-Final Office Action dated Jun. 7, 2010, for U.S. Appl. No. 11/237,461, filed Sep. 27, 2005, 8 pages. (5.01).
Non-Final Office Action dated Jun. 7, 2012, for U.S. Appl. No. 12/850,531, filed Aug. 4, 2010, 8 pages. (25015.04).
Non-Final Office Action dated Jun. 9, 2010, for U.S. Appl. No. 11/894,468, filed Aug. 20, 2007, 14 pages. (15.08).
Non-Final Office Action dated Jun. 9, 2020, for U.S. Appl. No. 16/141,627, filed Sep. 25, 2018, 7 pages.
Non-Final Office Action dated Mar. 12, 2007, for U.S. Appl. No. 11/232,190, filed Sep. 20, 2005, 11 pages. (15.26).

(56) References Cited

OTHER PUBLICATIONS

Non-Final Office Action dated Mar. 14, 2012, for U.S. Appl. No. 12/576,955, filed Oct. 9, 2009, 7 pages. (40.00) Termination Only.
Non-Final Office Action dated Mar. 15, 2012, for U.S. Appl. No. 12/690,109, filed Jan. 19, 2010, 7 pages. (42.00).
Non-Final Office Action dated Mar. 16, 2010, for U.S. Appl. No. 11/894,340, filed Aug. 20, 2007, 14 pages. (15.04).
Non-Final Office Action dated Mar. 18, 2009, for U.S. Appl. No. 10/901,554, filed Jul. 27, 2004, 12 pages. (15.23).
Non-Final Office Action dated Mar. 2, 2007, for U.S. Appl. No. 10/927,784, filed Aug. 27, 2004, 13 pages. (12.00).
Non-Final Office Action dated Mar. 27, 2008, for U.S. Appl. No. 10/900,980, filed Jul. 27, 2004, 7 pages. (15.24).
Non-Final Office Action dated Mar. 27, 2009, for U.S. Appl. No. 10/741,130, filed Dec. 19, 2003, 9 pages. (15.20).
Non-Final Office Action dated Mar. 29, 2010, for U.S. Appl. No. 11/894,463, filed Aug. 20, 2007, 14 pages. (15.07).
Non-Final Office Action dated Mar. 31, 2009, for U.S. Appl. No. 10/792,681, filed Mar. 2, 2004, 15 pages. (15.21).
Non-Final Office Action dated Mar. 31, 2009, for U.S. Appl. No. 11/237,461, filed Sep. 27, 2005, 6 pages. (5.01).
Non-Final Office Action dated Mar. 5, 2009, for U.S. Appl. No. 11/202,474, filed Aug. 11, 2005, 10 pages. (15.25).
Non-Final Office Action dated May 27, 2011, for U.S. Appl. No. 12/131,831, filed Jun. 2, 2008, 7 pages. (12.01).
Non-Final Office Action dated Nov. 14, 2007, for U.S. Appl. No. 10/741,130, filed Dec. 19, 2003, 8 pages. (15.20).
Non-Final Office Action dated Nov. 14, 2007, for U.S. Appl. No. 11/137,833, filed May 24, 2005, 8 pages. (15.02).
Non-Final Office Action dated Nov. 15, 2006, for U.S. Appl. No. 11/137,833, filed May 24, 2005, 12 pages. (15.02).
Non-Final Office Action dated Nov. 17, 2010, for U.S. Appl. No. 12/131,841, filed Jun. 2, 2008, 10 pages. (5.11).
Non-Final Office Action dated Nov. 23, 2010, for U.S. Appl. No. 11/583,627, filed Oct. 18, 2006, 13 pages. (28.00).
Non-Final Office Action dated Nov. 24, 2010, for U.S. Appl. No. 10/900,980, filed Jul. 27, 2004, 8 pages. (15.24).
Non-Final Office Action dated Nov. 24, 2015, for U.S. Appl. No. 14/156,347, filed Jan. 15, 2014, 5 pages (5.06).
Non-Final Office Action dated Nov. 26, 2008, for U.S. Appl. No. 11/201,949, filed Aug. 10, 2005, 7 pages. (25.00).
Non-Final Office Action dated Nov. 28, 2006, for U.S. Appl. No. 10/901,019, filed Jul. 27, 2004, 20 pages. (15.01).
Non-Final Office Action dated Nov. 30, 2006, for U.S. Appl. No. 10/776,682, filed Feb. 10, 2004, 14 pages. (5.10).
Non-Final Office Action dated Nov. 7, 2014, for U.S. Appl. No. 12/187,331, filed Aug. 6, 2008, 8 pages. (25015.03).
Non-Final Office Action dated Oct. 1, 2009, for U.S. Appl. No. 11/201,949, filed Aug. 10, 2005, 10 pages. (25.00).
Non-Final Office Action dated Oct. 12, 2010, for U.S. Appl. No. 12/131,831, filed Jun. 2, 2008, 6 pages. (12.01).
Non-Final Office Action dated Oct. 13, 2011, for U.S. Appl. No. 12/187,331, filed Aug. 6, 2008, 5 pages. (25015.03).
Non-Final Office Action dated Oct. 18, 2011, for U.S. Appl. No. 10/741,130, filed Dec. 19, 2003, 9 pages. (15.20).
Non-Final Office Action dated Oct. 18, 2011, for U.S. Appl. No. 10/776,682, filed Feb. 10, 2004, 7 pages. (5.10).
Non-Final Office Action dated Oct. 18, 2011, for U.S. Appl. No. 12/132,161, filed Jun. 3, 2008, 15 pages. (15.11).
Non-Final Office Action dated Oct. 19, 2007, for U.S. Appl. No. 11/202,474, filed Aug. 11, 2005, 7 pages. (15.25).
Non-Final Office Action dated Oct. 19, 2009, for U.S. Appl. No. 10/901,019, filed Jul. 27, 2004, 21 pages. (15.01).
Non-Final Office Action dated Oct. 2, 2009, for U.S. Appl. No. 11/237,461, filed Sep. 27, 2005, 7 pages. (5.01).
Non-Final Office Action dated Oct. 20, 2011, for U.S. Appl. No. 12/824,051, filed Jun. 25, 2010, 8 pages. (17.10).
Non-Final Office Action dated Oct. 23, 2006, for U.S. Appl. No. 10/776,682, filed Feb. 10, 2004, 14 pages. (5.10).
Non-Final Office Action dated Oct. 24, 2008, for U.S. Appl. No. 10/901,019, filed Jul. 27, 2004, 11 pages. (15.01).
Non-Final Office Action dated Oct. 25, 2010, for U.S. Appl. No. 11/202,474, filed Aug. 11, 2005, 8 pages. (15.25).
Non-Final Office Action dated Oct. 29, 2007, for U.S. Appl. No. 10/901,019, filed Jul. 27, 2004, 10 pages. (15.01).
Non-Final Office Action dated Oct. 29, 2010, for U.S. Appl. No. 11/894,530, filed Aug. 20, 2007, 11 pages. (15.09).
Non-Final Office Action dated Oct. 3, 2013, for U.S. Appl. No. 10/776,682, filed Feb. 10, 2004, 7 pages. (5.10).
Non-Final Office Action dated Oct. 8, 2009, for U.S. Appl. No. 10/901,455, filed Jul. 27, 2004, 10 pages. (17.00).
Non-Final Office Action dated Oct. 8, 2010, for U.S. Appl. No. 11/894,368, filed Aug. 20, 2007, 10 pages. (15.05).
Non-Final Office Action dated Sep. 14, 2010, for U.S. Appl. No. 11/201,949, filed Aug. 10, 2005, 10 pages. (25.00).
Non-Final Office Action dated Sep. 15, 2015, for U.S. Appl. No. 14/052,593, filed Oct. 11, 2013, 8 pages. (47.01).
Non-Final Office Action dated Sep. 17, 2009, for U.S. Appl. No. 10/656,797, filed Sep. 4, 2003, 13 pages. (15.00).
Non-Final Office Action dated Sep. 26, 2008, for U.S. Appl. No. 11/414,657, filed Apr. 27, 2006, 11 pages. (15.03).
Non-Final Office Action dated Sep. 3, 2020, for U.S. Appl. No. 16/211,109, filed Dec. 5, 2018, 14 pages.
Non-Final Office Action (Supplementary) dated May 9, 2008, for U.S. Appl. No. 11/255,400, filed Oct. 20, 2005, 7 pages. (15.27).
Notice of Allowance dated Aug. 16, 2018, for U.S. Appl. No. 15/265,781, filed Sep. 14, 2016, 7 pages.
Notice of Allowance dated Apr. 28, 2010, for U.S. Appl. No. 10/901,019, filed Jul. 27, 2004, 7 pages.
Notice of Allowance dated Aug. 30, 2012, for U.S. Appl. No. 12/133,319, filed Jun. 4, 2008, 8 pages.
Notice of Allowance dated Aug. 4, 2009, for U.S. Appl. No. 10/901,555, filed Jul. 27, 2004, 7 pages. (15.22).
Notice of Allowance dated Dec. 19, 2017, for U.S. Appl. No. 14/626,826, filed Feb. 19, 2015, 8 pages.
Notice of Allowance dated Dec. 24, 2020, for U.S. Appl. No. 16/058,847, filed Aug. 8, 2018, 8 pages.
Notice of Allowance dated Dec. 30, 2019, for U.S. Appl. No. 15/474,877, filed Mar. 30, 2017, 8 pages.
Notice of Allowance dated Dec. 6, 2010, for U.S. Appl. No. 12/132,375, filed Jun. 3, 2008, 9 pages. (15.10).
Notice of Allowance dated Feb. 20, 2020, for U.S. Appl. No. 15/817,015, filed Nov. 17, 2017, 7 pages.
Notice of Allowance dated Feb. 24, 2010, for U.S. Appl. No. 10/656,797, filed Sep. 4, 2003, 8 pages. (15.00).
Notice of Allowance dated Feb. 24, 2020, for U.S. Appl. No. 15/955,564, filed Apr. 17, 2018, 9 pages.
Notice of Allowance dated Jan. 3, 2020, for U.S. Appl. No. 14/868,290, filed Sep. 28, 2015, 6 pages.
Notice of Allowance dated Jul. 26, 2011, for U.S. Appl. No. 11/894,530, filed Aug. 20, 2007, 10 pages. (15.09).
Notice of Allowance dated Jun. 11, 2012, for U.S. Appl. No. 10/741,130, filed Dec. 19, 2003, 9 pages.—(15.20).
Notice of Allowance dated Jun. 15, 2016, for U.S. Appl. No. 14/156,347, filed Jan. 15, 2014, 7 pages.
Notice of Allowance dated Jun. 22, 2018, for U.S. Appl. No. 15/265,781, filed Sep. 14, 2016, 7 pages.
Notice of Allowance dated Jun. 8, 2012, for U.S. Appl. No. 11/894,401, filed Aug. 20, 2007, 9 pages. (25015.01).
Notice of Allowance dated Mar. 1, 2017, for U.S. Appl. No. 14/033,369, filed Sep. 20, 2013, 10 pages.
Notice of Allowance dated Mar. 2, 2015, for U.S. Appl. No. 12/187,331, filed Aug. 6, 2008, 5 pages. (25015.03).
Notice of Allowance dated Mar. 29, 2010, for U.S. Appl. No. 10/901,444, filed Jul. 27, 2004, 7 pages.
Notice of Allowance dated Mar. 31, 2014, for U.S. Appl. No. 12/576,955, filed Oct. 9, 2009, 8 pages. (40.00).
Notice of Allowance dated May 5, 2010, for U.S. Appl. No. 10/901,455, filed Jul. 27, 2004, 8 pages. (17.00).
Notice of Allowance dated Nov. 17, 2010, for U.S. Appl. No. 11/232,190, filed Sep. 20, 2005, 11 pages. (15.26).

(56) References Cited

OTHER PUBLICATIONS

Notice of Allowance dated Nov. 6, 2012, for U.S. Appl. No. 11/583,627, filed Oct. 18, 2006, 7 pages. (28.00).
Notice of Allowance dated Nov. 8, 2017, for U.S. Appl. No. 13/820,447, filed Oct. 18, 2013, 8 pages.
Notice of Allowance dated Oct. 29, 2015, for U.S. Appl. No. 10/901,554, filed Jul. 27, 2004, 8 pages.
Notice of Allowance dated Sep. 25, 2013, for U.S. Appl. No. 12/132,161, filed Jun. 3, 2008, 12 pages.—(15.11).
Notice of Allowance dated Sep. 30, 2020, for U.S. Appl. No. 16/141,627, filed Sep. 25, 2018, 8 pages.
Notice of Reasons for Rejection dated Jul. 24, 2012, for Japanese Patent Application No. 2008-526078, filed on Aug. 2, 2006, six pages. (English Translation).
Partial Supplementary European Search Report dated Apr. 30, 2020 for EP Application No. 17871289.9. 10 pages.
Saito, E. et al. (2010). "Experimental and computational characterization of designed and fabricated 50:50 PLGA porous scaffolds for human trabecular bone applications," J. Mater Sci. Mater Med. 21:2371-2383.
Shumay, S.J. et al. (Dec. 1988). "A 'Designer' Annuloplasty Ring for Patients with Massive Mitral Annular Dilatation," Ann. Thorac. Surg. 46(6):695-696.
Supplementary European Search Report dated Apr. 4, 2011, for EP Patent Application No. 03739139.8, filed on Jun. 13, 2003, 3 pages. (5.41).
Supplementary European Search RepoRT dated Nov. 10, 2008, for EP Application No. 04 78 2847, filed on Sep. 1, 2004, 2 pages. (15.43).
Towne, W.D. (Jan. 1973). "Letter to the Editor: Classification of Chordae Tendineae," Circulation 47:209.
U.S. Appl. No. 11/875,774, filed Oct. 19, 2007, by Serina et al. (31.00—converted to provisional—never published).
U.S. Appl. No. 12/131,831, filed Jun. 2, 2008, by Starksen et al. (12.01).
U.S. Appl. No. 12/131,841, filed Jun. 2, 2008, by Morales et al. (5.11).
U.S. Appl. No. 12/132,328, filed Jun. 3, 2008, by Morales et al. (5.02).
U.S. Appl. No. 12/133,306, filed Jun. 4, 2008, by Starksen et al. (16.01).
U.S. Appl. No. 12/133,319, filed Jun. 4, 2008, by Starksen et al. (16.02).
U.S. Appl. No. 14/052,593, filed Oct. 11, 2013, by Serina et al.—(47.01); Issued.
U.S. Appl. No. 11/656,141, filed Jan. 19, 2007, by Straksen et al. (1.00).
U.S. Appl. No. 11/894,340, filed Aug. 20, 2007, by To et al. (15.04).
U.S. Appl. No. 11/894,368, filed Aug. 20, 2007, by To et al. (15.05).
U.S. Appl. No. 11/894,397, filed Aug. 20, 2007, by To et al. (15.06).
U.S. Appl. No. 11/894,401, filed Aug. 20, 2007, by To et al. (25015.01).
U.S. Appl. No. 11/894,463, filed Aug. 20, 2007, by To et al. (15.07).
U.S. Appl. No. 11/894,468, filed Aug. 20, 2007, by To et al. (15.08).
U.S. Appl. No. 11/894,530, filed Aug. 20, 2007, by To et al. (15.09).
U.S. Appl. No. 12/132,161, filed Jun. 3, 2008, by Starksen et al. (15.11).
U.S. Appl. No. 12/132,375, filed Jun. 3, 2008, by Starksen et al. (15.10).
U.S. Appl. No. 12/187,331, filed Aug. 6, 2008, by To et al. (25015.03).
U.S. Appl. No. 12/480,568, filed Jun. 8, 2009, by Serina et al. (20031.01).
U.S. Appl. No. 12/576,955, filed Oct. 9, 2009, by Hernlund et al. (20040.00).
U.S. Appl. No. 12/577,044, filed Oct. 9, 2009, by Meier et al. (20037.00).
U.S. Appl. No. 12/581,040, filed Oct. 16, 2009, by Starksen et al. (20015.12).
U.S. Appl. No. 12/850,531, filed Aug. 4, 2010, by Starksen et al. (25015.04) Published.
U.S. Appl. No. 13/042,369, filed Mar. 7, 2011, by Starksen et al. (15.13).
U.S. Appl. No. 16/211,109, filed Dec. 5, 2018, by Serina et al.
U.S. Patent Prosecution File History U.S. Appl. No. 60/128,690, filed Apr. 9, 1999 in the United States Patent and Trademark Office.
U.S. Appl. No. 61/083,109, filed Jul. 23, 2008, by Johansson. (30004.00).
U.S. Appl. No. 61/104,681, filed Oct. 10, 2008, by Serina et al. (30037.00).
U.S. Appl. No. 61/104,686, filed Oct. 10, 2008, by To et al. (30040.00).
U.S. Appl. No. 61/145,964, filed Jan. 20, 2009, by Fabro. (30042.00).
U.S. Appl. No. 61/160,018, filed Mar. 13, 2009, by Johansson. (30048.00).
U.S. Appl. No. 61/160,230, filed Mar. 13, 2009, by Meier et al.
U.S. Appl No. 61/160,670, filed Mar. 16, 2009, by Fabro et al. (30029.00).
U.S. Appl. No. 61/178,910, filed May 15, 2009, by Serina et al. (30051.00).
U.S. Appl. No. 61/178,938, filed May 15, 2009, by Fabro. (30050.00).
Written Opinion of the International Searching Authority dated Dec. 19, 2006, for PCT Application No. PCT/US2006/031190, filed Aug. 10, 2006, 6 pages.
Written Opinion of the International Searching Authority dated Apr. 2, 2007, for PCT Application No. PCT/US2006/043597, filed Nov. 8, 2006, 7 pages.
Written Opinion of the International Searching Authority dated Dec. 10, 2009, for PCT Patent Application No. PCT/US2009/060202, filed on Oct. 9, 2009, 10 pages. (37.40).
Written Opinion of the International Searching Authority dated Feb. 15, 2007, for PCT Application No. PCT/US2006/035933, filed on Sep. 15, 2006, 4 pages.
Written Opinion of the International Searching Authority dated Feb. 21, 2012, for PCT Patent Application No. PCT/US2011/050331, filed on Sep. 2, 2011, 4 pages.—(53.40).
Written Opinion of the International Searching Authority dated Jan. 12, 2010, for PCT Patent Application No. PCT/US2009/60227, filed on Oct. 9, 2009, 5 pages. (40.40).
Written Opinion of the International Searching Authority dated Mar. 19, 2010, for PCT Patent Application No. PCT/US/2010/021437, filed on Jan. 19, 2010, 8 pages. (47.40).
Written Opinion of the International Searching Authority dated Mar. 7, 2007, for PCT Patent Application No. PCT/US2004/028431, filed on Sep. 1, 2004, 4 pages.—(15.40).
Written Opinion of the International Searching Authority dated Mar. 8, 2018, for PCT Patent Application No. PCT/US2017/062382, filed on Nov. 17, 2017, 10 pages.
Written Opinion of the International Searching Authority dated Mar. 9, 2010, for PCT Patent Application No. PCT/US/2010/021440, filed on Jan. 19, 2010, 5 pages. (042).
Written Opinion of the International Searching Authority dated May 19, 2009, for PCT Patent Application No. PCT/US2008/080381, filed on Oct. 17, 2008, 10 pages. (31.40).
Written Opinion of the International Searching Authority dated May 21, 2008, for PCT Application No. PCT/US2008/000351, filed on Jan. 9, 2008, 6 pages. (1.40) cite in 15.03 only.

\* cited by examiner

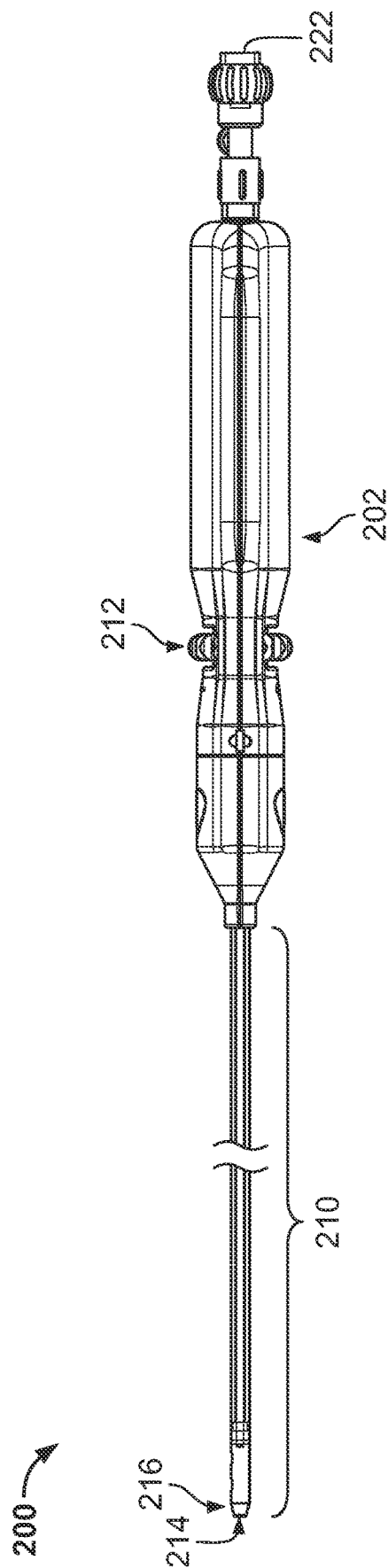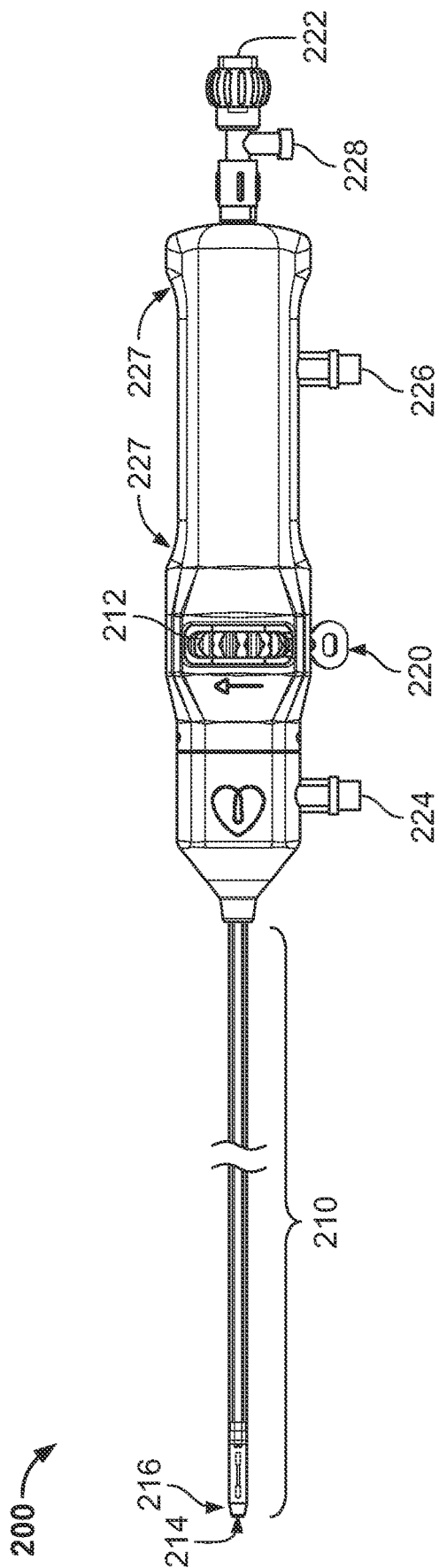
FIG. 2A
FIG. 2B

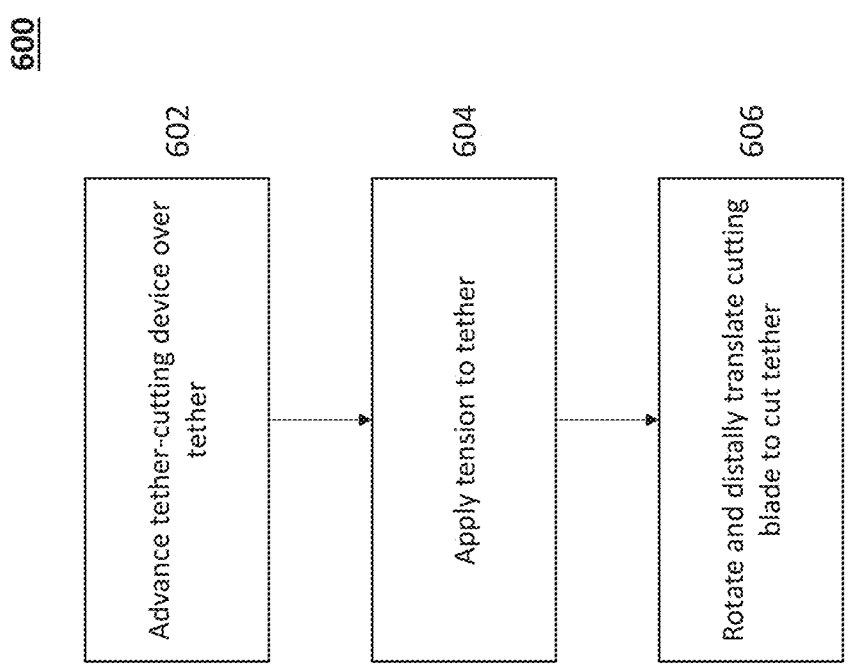

DEVICES AND METHODS FOR TETHER CUTTING

CROSS-REFERENCE TO RELATED APPLICATIONS

This application claims priority to U.S. Provisional Patent Application No. 62/874,279, filed Jul. 15, 2019, which is hereby incorporated by reference in its entirety.

TECHNICAL FIELD

The devices and methods described herein relate generally to termination of tethers that have been deployed to a target site in a body of a subject. More specifically, the devices and methods described herein related to cutting such tethers after they have been secured.

BACKGROUND

Many types of medical procedures involve the use of tethers. For example, a tether may be used to bring together two or more tissue regions. The tether may then be secured to maintain the compression or tension applied to the tissue region by the tether, and extra tether may be cut or removed. However, consistently cutting a tether can be difficult, as the tether often needs to be cut at or near the target site in the body of the subject and tethers used to secure tissue are generally very strong. Current devices and methods of cutting a tether are often unreliable and may fail to fully cut the tether, or may prematurely cut the tether before the device is positioned. Further, certain devices or methods may cut the tether at more than one point, resulting in the formation of loose pieces of tether.

Accordingly, it would be desirable to provide devices that can be placed simply and effectively at a target site, and methods for effectively cutting a tether after the tether has been deployed at the target site and secured. It would further be desirable for such methods and devices to be efficient and reliable, and to have a way of protecting the tether from being cut until the operator is ready. Further, it would be desirable for devices and methods to cut the tether in only one place to avoid the need for an additional step of retrieving loose pieces of tether.

SUMMARY

Described herein are devices and methods for cutting a tether, such as a tether that has been used to tighten or compress tissue (e.g., by pulling two or more sections or pieces of tissue together). Devices described herein generally include a catheter, an inner shaft, and a cutting blade. The inner shaft may be coaxial with the cutting blade, and both the inner shaft and cutting blade may be coaxially arranged within the catheter lumen. For example, the inner shaft may be disposed within the lumen of the catheter, and the cutting blade may be disposed over the inner shaft. The catheter may comprise a proximal end, a distal end, a lumen therethrough, and a sidewall, where the sidewall comprises a first opening and a second opening distal to the first opening. The lumen of the catheter may terminate in a distal opening. The inner shaft may comprise a proximal end, a distal end, and a shaft lumen therethrough, where the inner shaft is disposed within the lumen of the catheter proximal to the first opening. The cutting blade may be disposed over the inner shaft, and an actuation mechanism may be coupled to the cutting blade and configured to rotate and translate the cutting blade about the inner shaft.

In some variations, the inner shaft may be stationary within the lumen of the catheter. In other variations, the inner shaft may be moveable within the lumen of the catheter. A lead screw may be coupled to the inner shaft, where rotation of the lead screw translates the inner shaft. An actuation mechanism may be coupled to the lead screw, such that moving the actuation mechanism turns the lead screw. In some variations, a gear mechanism may be coupled to the inner shaft, where rotation of the gear rotates and/or translates the inner shaft. In some variations, the distal end of the inner shaft may be blunt.

Tether-cutting devices described herein may further comprise a first configuration where a distal end of the blade is proximal to the distal end of the inner shaft, and a second configuration where the distal end of the blade is distal to the distal end of the inner shaft. Devices may comprise an actuation mechanism configured to move the blade between the first and second configurations in order to cut a tether. In some variations, a tether may extend across a portion of the catheter lumen into the lumen of the inner shaft. For example, a tether extending from the second opening, through the first opening, and through the shaft lumen, may extend partially across the lumen of the catheter. The cutting blade may be rotatable and longitudinally translatable over the inner shaft in order to cut the tether. In some variations, the blade may be tubular.

Tether-cutting devices described herein may further comprise a proximal handle. The proximal handle may comprise an actuation mechanism to move the blade between the first and second configurations, for example. The actuation mechanism may comprise a lead screw coupled to the blade, where rotation of the screw rotates and longitudinally translates the blade. For example, the actuation mechanism may be configured to simultaneously slide the blade along the length of the catheter, and rotate the blade about a longitudinal axis of the catheter. In some variations, the actuation mechanism may be configured to bidirectionally move the blade distally and proximally within the catheter. In some variations, the blade may be retained within the lumen of the catheter by the actuation mechanism.

Also described herein are methods of cutting a tether. Methods may comprise advancing a tether-cutting device over a tether, applying tension to the tether, and simultaneously rotating and distally translating a cutting blade of the tether-cutting device to cut a portion of the tether that extends partially across a lumen of a catheter of the tether-cutting device. In some variations, advancing a tether-cutting device over a tether may also include loading the tether into the various components of the device. The tether-cutting device advanced over the tether may comprise a catheter, an inner shaft, and a cutting blade disposed over the inner shaft. The catheter may comprise a lumen and a sidewall, where the sidewall may comprise a first opening, and a second opening distal to the first opening. The inner shaft may comprise a shaft lumen, and the inner shaft may be disposed within the lumen of the catheter. The device may further comprise a cutting blade disposed over the inner shaft. In some variations, the blade and the inner shaft may be coaxial. In some variations, a tether may extend from the second opening, through the first opening, and through the shaft lumen such that a portion of the tether extends partially across the lumen of the catheter. In some variations, simultaneously rotating and distally translating the blade comprises actuating an actuation mechanism coupled to the cutting blade. The actuation mechanism may be in a proximal handle. Rotating and distally translating the blade may comprise moving the blade from the first position to the second position.

Methods described herein may further comprise proximally translating the blade. In some variations, methods of cutting a tether may further comprise actuating the blade to move from a first position in which a distal end of the blade is proximal to a distal end of the inner shaft, to a second position in which the distal end of the blade is distal to the distal end of the inner shaft. In some variations, the blade may remain in a first position until actuated using the actuation mechanism. Methods may also comprise adjusting an angle of the tether prior the cutting the tether. A length of a tether that extends from the first opening into the shaft lumen forms an angle with respect to a longitudinal axis of the shaft lumen. Methods may comprise adjusting the angle to a first pre-selected angle value prior to advancing the tether-cutting device over the tether, and adjusting the angle to a second pre-selected angle value prior to cutting the tether. In some variations, the second pre-selected angle value may be greater than the first pre-selected angle value. Adjusting the angle to the first pre-selected angle value may comprise proximally translating the inner shaft. Adjusting the angle to the second pre-selected angle value may comprise distally translating the inner shaft. In some variations of methods described herein, the tether is a component of a heart implant that has been secured in a heart at an implant site, and the method of cutting a tether may further comprise advancing the tether-cutting device to the implant site. The implant may be a valve repair device comprising anchors affixed to tissue and coupled to a tether

BRIEF DESCRIPTION OF THE DRAWINGS

The drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 2A and 2B depict one variation of a tether-cutting device;

FIG. 3C depicts a schematic front cross sectional view of a variation of a tether-cutting device taken along line 3C-3C of FIG. 3A;

FIG. 6 depicts a flowchart representation of one variation of a method for cutting a tether.

DETAILED DESCRIPTION

Figure 1A:
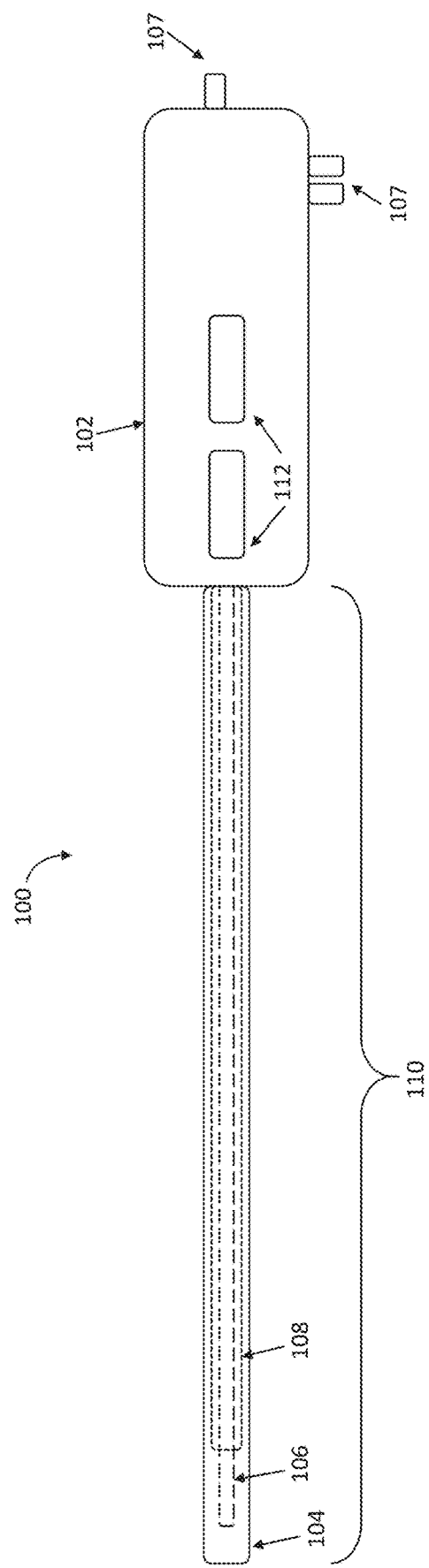
FIGS. 1A and 1B depict schematic representations of one variation of a tether-cutting device.

The following description is not intended to limit the devices and methods described herein to these variations. Variations, configurations, implementations, example implementations, and examples described herein are optional and are not exclusive to the variations, configurations, implementations, exampled implementations, and examples they described. The devices and methods described herein can include any and all permutations of these variations, configurations, implementations, example implementations, and examples.

Described herein are devices and methods for cutting a tether. One variation of a tether-cutting device may comprise a catheter, an inner shaft, and a cutting blade. The inner shaft and the cutting blade may be coaxially arranged within the catheter lumen. The cutting blade may be movably disposed about the inner shaft (e.g., longitudinally translatable and/or rotatable over the inner shaft). The inner shaft may comprise a longitudinal lumen and may extend from a distal portion of the catheter to a proximal handle. In some variations, a tether may be extended across a portion of the catheter lumen into the lumen of the inner shaft. For example, the tether may extend from an opening in the sidewall of the catheter into the lumen of the inner shaft, and extend through the length of the inner shaft lumen to the proximal handle. The inner shaft may shield the tether from the cutting blade while the device is advanced over the tether to the desired cut location. The cutting blade may be rotatable and longitudinally translatable over the inner shaft in order to contact and cut the tether. Simultaneous translation and rotation of the cutting blade may create a shearing or slicing effect on the tether, which may help facilitate consistent and reliable cutting of the tether. In some variations, the proximal handle of a tether-cutting device may be coupled to the proximal ends of the catheter, inner shaft and cutting blade.

One variation of a method for cutting a tether may comprise threading a tether through a tether-cutting device such that the tether extends from an opening in the sidewall of a catheter into a lumen of an inner shaft disposed within the catheter lumen, and simultaneously rotating and translating a cutting blade disposed over the inner shaft to contact and cut the portion of the tether extending between the sidewall opening and the inner shaft lumen. In some variations, the method may comprise advancing a tether-cutting device over a tether, and holding the tether in tension prior to cutting the tether. Optionally, in some variations, the inner shaft may be moved proximally within the catheter lumen, which may help reduce the catheter tracking force and facilitate the advancement of the catheter. The method may further comprise using an actuation mechanism to the control the translation and rotation of the cutting blade to cut the tether. Simultaneous translation and rotation of the cutting blade may allow the cutting blade to apply a shearing force to slice through the tether, which may facilitate reliable cutting of the tether. The cutting blade may be translated such that it moves from a first position, in which a distal end of the cutting blade is proximal to a distal end of the inner shaft, to a second position, in which a distal end of the cutting blade (e.g. a sharpened edge) is distal to a distal end of the inner shaft. Optionally, in some variations, the inner shaft may be advanced distally (e.g., closer, but preferably not distal to, the proximal-most opening in the sidewall of the catheter) which may provide a more effective cutting angle between the tether and the cutting blade just prior to translating the cutting blade to contact the tether.

Devices

Tether-cutting devices described herein generally comprise a proximal handle attached to a catheter assembly comprising a catheter, an inner shaft and a cutting blade. The inner shaft and the cutting blade may be disposed coaxially within the lumen of the catheter. The proximal handle may comprise one or more actuation mechanisms configured to control the movement of the various components of the device, such as the cutting blade and/or the inner shaft. The cutting blade may be movably disposed over the inner shaft within the lumen of the catheter. The actuation mechanism may allow to operator to simultaneously rotate and translate the cutting blade about the inner shaft. The inner shaft may be configured to protect the tether from being cut by the catheter. When the cutting blade is in a first position in which a sharpened portion of the cutting blade is proximal to a distal end of the inner shaft, the inner shaft may retain the tether distal to the sharpened portion so that the tether is not cut. In order to cut the tether, the operator may actuate the cutting blade to move the cutting blade to a second position in which the sharpened portion of the cutting blade is distal to the distal end of the inner shaft. As the cutting blade is moved from the first position to the second position, the cutting blade may come into contact with and cut the tether.

FIG. 1A depicts a schematic view of one variation of a tether-cutting device (100). The tether-cutting device (100) may comprise a proximal handle (102), attached to a catheter assembly (110) comprising a catheter (104), an inner shaft (106), and a cutting blade (108). The cutting blade (108) and the inner shaft (106) are disposed coaxially within the lumen of the catheter (104). A tether may extend across a portion of the catheter lumen, for example, from an opening in sidewall of the catheter (104) into a lumen of the inner shaft (106). In some variations, the tether may be held in tension outside of the proximal handle, which may help facilitate cutting the tether. The proximal handle (102) may comprise one or more actuation mechanisms (112) to control the various components of the device, for example, movement of the cutting blade (108) within the catheter lumen. For example, an actuation mechanism may be coupled to the cutting blade (108) and configured to move it from its first position in the first configuration to its second position in the second configuration. In some variations, a safety tab may be coupled to the actuation mechanism (112) to prevent the actuation mechanism from being moved, and/or to prevent movement of the cutting blade until the operator is ready to cut the tether. By holding the cutting blade stationary in the lumen of the catheter until the tether is ready to be cut, the safety tab helps protect the tether from being prematurely cut. Optionally, the proximal handle may comprise additional actuation mechanisms (112) that are configured to control movement of the inner shaft (106) within the catheter lumen. The proximal handle (102) may further comprise various ports (107) to allow for exit and entry of various devices and/or substances through the catheter. For example, the proximal handle may comprise a port through which the tether may be threaded to exit the catheter at the proximal end. The proximal handle may also include various flush ports that allow the operator to introduce fluids, such as saline solution, into various components of the device. For example, the proximal handle may comprise ports to deliver fluids into the lumen of the catheter, the inner shaft, and/or the cutting blade. Any of the ports described above may allow for introduction of fluids (e.g. saline solution, contrast agents, medicaments), and/or the introduction of devices (e.g. implant delivery devices, catheters, imaging devices) into the lumen of any or all of the components of the catheter assembly.

Figure 1B:
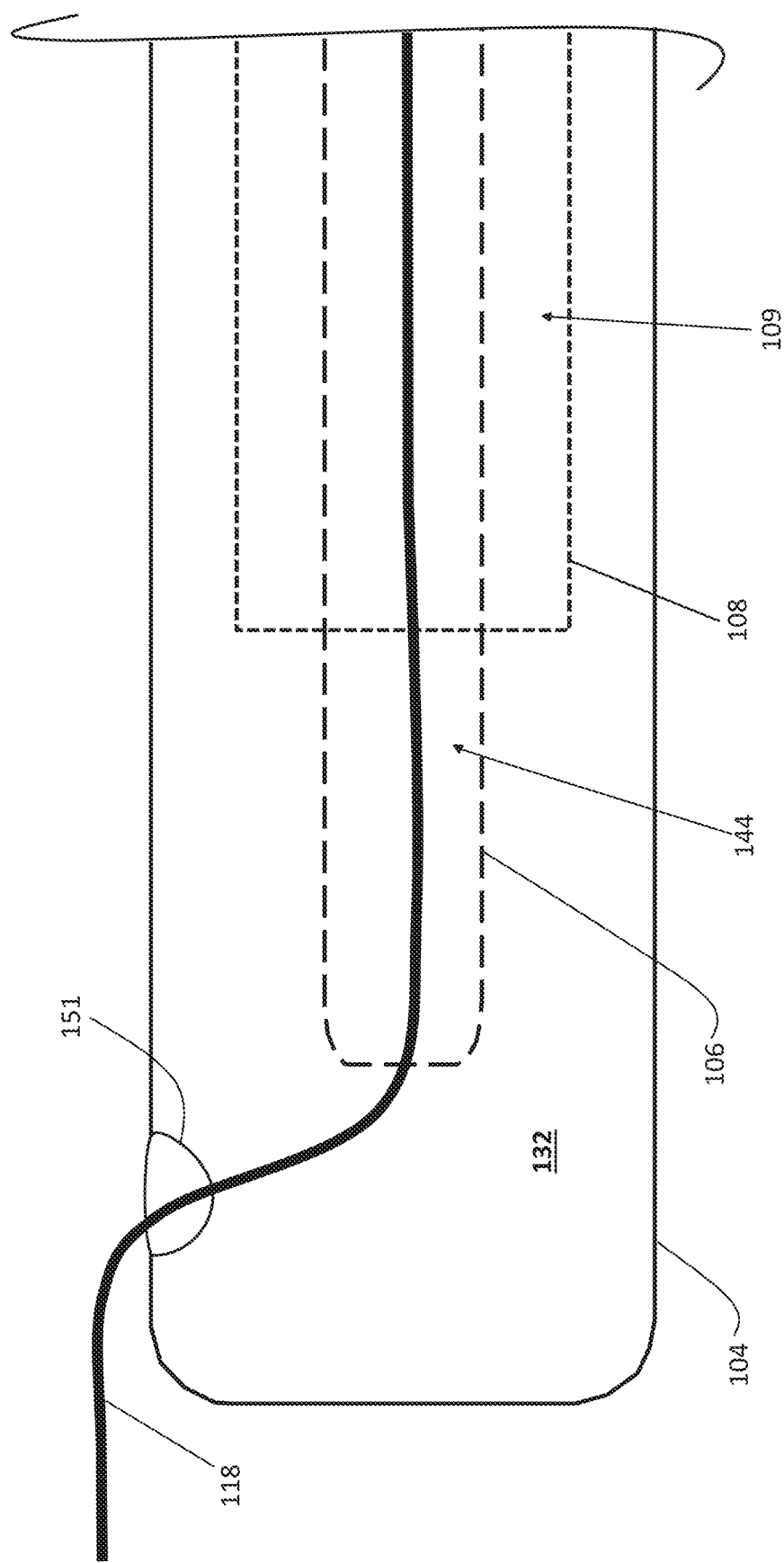

FIG. 1B is a schematic depiction of one example of a tether threaded through a tether-cutting device. As depicted there, the tether-cutting device may comprise a catheter (106) having a proximal end, a distal end, a catheter lumen (132) and an opening (151) in its sidewall, an inner shaft (106) and a cutting blade (108) that is disposed over the inner shaft (106). The catheter lumen (132) may extend between the proximal and distal ends. The inner shaft (106) may comprise a proximal end, a distal end and an inner shaft lumen (144) that extends between the proximal and distal ends. The cutting blade (108) may comprise a proximal end, a distal end and a cutting blade lumen (109) that extends between the proximal and distal ends. The cutting blade (108) may be slidably disposed about the inner shaft (106). The inner shaft (106) may be disposed within the cutting blade lumen (109), and the cutting blade (108) may be disposed within the catheter lumen (132) such that the catheter, the inner shaft, and the cutting blade are oriented coaxially. That is, the central longitudinal axes of each of the catheter, the inner shaft, and the cutting blade are substantially aligned with each other. In some variations, the catheter may comprise two or more sidewall openings. A tether (118) may extend across a portion of the catheter lumen (132) between the sidewall opening (151) and the inner shaft lumen (144). The tether (118) may extend through the entire length of the inner shaft lumen to the proximal handle (not shown in FIG. 1B). The cutting blade may be rotatable and longitudinally translatable over the inner shaft in order to contact and cut the tether.

The tether-cutting device may comprise a first configuration and a second configuration. In the first configuration, the cutting blade may be retained in a location that is proximal to a distal end of the inner shaft. For example, as depicted in FIG. 1B, the sharpened portion of the cutting blade (e.g., the distal-most end), is located proximal to the distal end of the inner shaft (106). In this first configuration, the sharpened portion of the cutting blade does not contact and/or cut the portion of the tether (118) that extends between the inner shaft lumen (144) and the sidewall opening (151). This may help reduce the risk of unintentionally cutting the tether, for example, while the tether-cutting device is being advanced over the tether to the desired cut position. In the second configuration, the cutting blade (108) may be located distal to the distal end of the inner shaft (106). As the cutting blade (108) translates distally from a first location in the first configuration (i.e., a location that is proximal to the distal end of the inner shaft) to a second location in the second configuration (i.e., a location that is distal to the distal end of the inner shaft), it may contact and cut the tether (118). That is, as the cutting blade (108) moves distally, it may contact and cut the portion of the tether (118) that extends between the sidewall opening (151) and the inner shaft lumen (144). In some variations, the cutting blade (108) may be simultaneously rotated and distally translated as the device transitions from the first configuration to the second configuration. Rotating and longitudinally translating the cutting blade may provide a shear force that facilitates reliable and complete cutting of the tether.

While the variation of the tether-cutting device depicted in FIG. 1B has one sidewall opening in the catheter, optionally, in some variations, the catheter may further comprise an opening at a distal end, and a second sidewall opening. The second sidewall opening may be distal to the first sidewall opening. In some variations, the tether may be threaded into the catheter lumen through the distal opening, out of the catheter lumen through the second sidewall opening, and back into the catheter lumen through the first sidewall opening. The tether may then be threaded from the first sidewall opening and into the lumen of the inner shaft such that it crosses a portion of the catheter lumen, as described above. The tether may then extend proximally along the entire length of the inner shaft to the proximal handle of the tether-cutting device and may exit the handle at a tether port.

FIGS. 2A and 2B depict an exemplary tether-cutting device (200). The tether-cutting device (200) may comprise a proximal handle (202) attached to a catheter assembly (210), including a catheter, an inner shaft, and a cutting blade. The catheter comprises an opening (214) at a distal end (216). The operator may thread a tether through the distal opening (214) at the distal end (216) of the catheter. The proximal handle (202) may comprise an actuation mechanism (212) used to control the movement of the components of the device. For example, the actuation mechanism (212) may be used to control the movement of the cutting blade within the lumen of the catheter. A safety tab (220) may be removably coupled to the actuation mechanism to prevent premature movement of one or more device components, such as the cutting blade. The proximal handle (202) may further comprise one or more ports to allow devices or substances to enter and exit the device. For example, a tether port (222) may allow a tether to exit the proximal handle. The proximal end of the tether extending through the port (222) may be held in tension by various mechanisms. For example, the proximal end of the tether may be attached to weights. The proximal handle (202) may further comprise various flush ports for introducing fluids into the various components of the device. For example, an outer flush port (224) may be in fluid communication with the catheter, an inner flush port (226) may be in fluid communication with the inner shaft, and a cutting blade flush port (228) may be in fluid communication with the cutting blade.

In some variations, the proximal handle coupled to the catheter assembly may be configured to allow the operator to control the operation of the tether-cutting device. Any suitable mechanism may be used to couple the catheter assembly to the proximal handle. For example, the catheter, the inner shaft, and the cutting blade may be held in place inside of the proximal handle by friction fit. In another example, non-movable components, such as the catheter and/or the inner shaft may be soldered or molded to the proximal handle. In another example, non-movable components may be secured to proximal handle using screws, brackets, or pins. The proximal handle may have an outer shell defining a substantially hollow inner body. Various components of the tether-cutting device may be housed within the inner body of the proximal handle. The handle may have a proximal portion comprising one or more contours that are configured to allow an operator to easily grip the handle. For example, the proximal portion of the outer shell may have one or more convex curves (e.g., contours (227) of FIG. 2B) to facilitate gripping of the handle, and may be sized such that a user can easily fit his or her hand to the handle. The outer shell may further comprise one or more indentations to provide for comfortable finger placement on the handle. The handle may be made of any suitable material. The proximal handle may further comprise various ports to accommodate the entry and exit of various devices and/or substances through the components of the tether-cutting device. For example, the proximal handle may comprise a port through which the tether exits the handle (e.g., tether port (222) of FIGS. 2A-2B). The proximal handle may also include various flush ports that allow the operator to introduce liquid, such as saline solution, into various components of the device. For example, an outer flush port may be in fluid communication with the catheter lumen in order to allow the operator to flush liquid through the catheter lumen. An inner flush port may be in fluid communication with the inner shaft in order to allow the operator to flush liquid through the inner shaft lumen. A cutter flush port may be in fluid communication with the lumen of the cutting blade in order to allow the operator to flush liquid through the cutting blade lumen. Various flush ports (e.g., ports (224, 226, 228) depicted in FIG. 2B) may allow entry or exit of liquids such as saline solution, contrast agents, medicaments, or any suitable liquid, into or out of the device. Further, any of the ports described above may also allow introduction of devices, such as implant delivery device, catheters, imaging devices, or any suitable device into the lumen of any of the components of the catheter system.

The outer shell of a proximal handle may comprise one or more openings to accommodate various components, such as buttons, dials, wheels, ports and/or structures that may be used to control operation of the device. For example, the outer shell may comprise an opening configured to house an actuation mechanism such that the operator can control an actuation mechanism while gripping the proximal handle. A portion of the actuation mechanism may protrude out of the opening in the outer shell while another portion may be housed within the inner body. The actuation mechanism maybe be in the form of a rotatable wheel that may be turned in order to move the cutting blade. However, the actuation mechanism may comprise any suitable configuration, such as rotatable sphere, a flat, rectangular band, or a rectangular or cylindrical notch. Further, the actuation mechanism may comprise any suitable cross section including ovular, triangular, square-shaped, or rectangular. The actuation mechanism need not be moved by rotation, but may instead be moved in any suitable manner, including sliding, pulling, or pushing. For example, the actuation mechanism may be in the form of a flat moveable belt or band that is coupled to the cutting blade, such that when the operator slides the belt the inner shaft is moved in a corresponding fashion. Alternatively or additionally, the actuation mechanism may be in the form of a sliding notch that is coupled to the cutting blade, such that when the operator slides the notch, the cutting blade is moved in a corresponding fashion. The actuation mechanism may also be in the form of a switch or button, such that pushing the switch or button may be used to facilitate the motion of the cutting blade. The actuation mechanism may be used to facilitate the movement of the cutting blade in any suitable manner.

In one variation, the actuation mechanism may be coupled to the cutting blade within the inner body of the proximal handle. The actuation mechanism may be coupled to a lead screw, and the lead screw may be coupled to the cutting blade such that when the actuation mechanism is turned the lead screw causes the cutting blade to move. The actuation mechanism may be coupled to the lead screw in any suitable manner, including those discussed below. The lead screw may be coupled to the cutting blade in any suitable manner. For example, the lead screw may be fixedly attached to the cutting blade such as by molding or soldering. The lead screw may act to facilitate movement of the cutting blade in any suitable fashion. For example, threading on an exterior surface of the lead screw may interact with a nut, such that as the actuation mechanism rotates the lead screw, the threading of the lead screw interacts with an interior surface of the nut, moving the set screw forward, thereby moving the cutting blade forward. Various mechanism may be used in the place of a lead screw to facilitate the movement of the cutting blade, as discussed below.

Various mechanisms, such as gears, a rack and pinion, a slider crank mechanism, a cam and roller, friction wheels, pulleys, or any other suitable mechanism may be employed to actuate the cutting blade. These mechanisms may directly actuate the cutting blade, or they may engage with a lead screw or other similar apparatus attached to the cutting blade to facilitate movement of the cutting blade. Although examples below describe a cutting blade interacting with various mechanisms to translate and/or rotate the cutting blade, similar configurations apply to variations in which the cutting blade is coupled to a lead screw, which may interact with any of the mechanisms described below in a similar manner. For example, gears may be used to translate and rotate the cutting blade. In one variation of the devices described herein, the actuation mechanism may be coupled to a gear, and the gear may be coupled to a threaded or notched surface on the cutting blade. Moving or turning the actuation mechanism turns the gear, and the gear engages the threading or notches on the surface of the cutting blade to move it forward and/or rotate it. For example, the cutting blade may comprise helical threading extending around and along a portion of the proximal end. When the protrusions of the actuation mechanism engage the threading, the cutting blade may be moved forward and rotated. In another variation, the cutting blade may comprise notches, indentations, or protrusions around a circumference. When the actuation mechanism engages the circumferentially aligned notches/indentations/protrusions, the cutting blade may rotate about an axis. In another variation, the cutting blade may comprise notches, indentations, or protrusions along the length of the cutting blade, such that when protrusions of the actuation mechanism engage the notches/protrusions/indentations of the cutting blade, the cutting blade is moved forward. A rack and pinion mechanism may also be used to translate and/or rotate the cutting blade. For example, the actuation mechanism may be coupled to, or act as, a gear such that when the user moves or turns the actuation mechanism it engages notches or threading on the cutting blade, converting the rotational motion of the actuation mechanism into linear and/or rotational motion of the cutting blade. A slider crank mechanism may also be used to translate and/or rotate the cutting blade. For example, the actuation mechanism may be coupled to a rotating crank such that when the actuation mechanism is moved, the crank is rotated. The crank may be coupled to a rod, which is coupled to the cutting blade, such that rotation of the crank slides the rod and cutting blade forward (or backward, depending on the direction of rotation). A cam and roller mechanism may also be used to rotate and/or translate the cutting blade. For example, the actuation mechanism may acts as, or be coupled to, a cam that rotates about an axis. As the cam rotates, it may engage and turn a roller, which is coupled to the cutting blade to rotate/and or translate it. Friction wheels may also be used to rotate and/or translate the cutting blade. For example, the actuation mechanism may be a friction wheel, and may be coupled to a second friction wheel with a different orientation. The second friction wheel may be frictionally or otherwise coupled to the cutting blade such that rotation of the second friction wheel translates and/or rotates the cutting blade. A pulley system may also be used to rotate and/or translate the cutting blade. For example, the actuation mechanism may be coupled to one or more pulleys, which are coupled to the cutting blade, such that rotation of the actuation mechanism pulls on rope or string connecting the pulleys, and the pulleys translate and/or rotate the cutting blade. Electronic actuation mechanisms may also be used to control the movement of the various components of this device, including the cutting blade. For example, the actuation mechanism may act as an on/off switch to a circuit. The circuit may be electronically connected to the cutting blade such that turning the on/off switch rotates and/or translates the cutting blade.

As discussed above, the tether-cutting devices described herein may comprise one or more actuation mechanisms to control one or more aspects of the movement of the cutting blade. One actuation mechanism may control both (e.g., simultaneous) rotation and translation of the cutting blade. However, in another variation, moving an actuation mechanism may only result in rotation of the cutting blade. Similarly, moving an actuation mechanism may result only in proximal or distal movement of the cutting blade. Multiple actuation mechanisms, each coupled to the cutting blade in any suitable manner, could be used to control the movement of the cutting blade, such that rotation and translation of the cutting blade are controlled by separate actuation mechanisms. In one variation, one actuation mechanism may be coupled to the blade such that movement of the actuation mechanism translates to linear motion, while a separate actuation mechanism may be coupled to the blade such that movement of the actuation mechanism controls rotational motion. For example, a first actuation mechanism may be coupled to gear, and the gear may be coupled to a rod and crank such that turning the gear results in linear motion of the blade. A second actuation mechanism may be coupled to a gear that engages notches, indentations, or threading on the outer surface of the lead screw or cutting blade to rotate the cutting blade about an axis, such that turning the gear results in rotational motion of the blade. Any suitable mechanism may be used to separately control the rotational and translation motion of the cutting blade, including those discussed above in relation to controlling simultaneous rotation and translation. Further, proximal and distal movement of the cutting blade may be controlled by separate mechanisms. For example, a first actuation mechanism may be coupled to a first one way gear that translates the blade only distally. A second actuation mechanism may be coupled to a second one way year that translates the blade only proximally. Any suitable mechanism may be used to separately control the proximal and distal translation of the cutting blade, including those discussed above.

The proximal handle may also comprise a safety tab removably coupled to the actuation mechanism. The safety tab may be used to hold the actuation mechanism stationary, thereby preventing the movement of components of the device. Various configurations of safety tabs are described below. In some variations, a safety tab is removably coupled to the proximal handle configured to hold the cutting blade in place. The safety tab may physically interfere with the actuation mechanism to prevent it from turning, thereby preventing the cutting blade from moving. For example, the actuation mechanism may comprise a series of protrusions, and the safety tab may be inserted into the proximal handle between two of the protrusions of the actuation mechanism to prevent the actuation mechanism from being moved.

Any suitable mechanism may be employed to prevent the actuation mechanism from turning. For example, the safety tab could comprise a small cylindrical or rectangular pin that fits into a corresponding opening in the actuation mechanism and the proximal handle. Inserting the pin-like safety tab into the proximal handle and actuation mechanism may prevent the actuation mechanism from turning. Further, any suitable mechanism can be used to hold the cutting blade in place in the lumen of the catheter until the operator is ready to move the blade to cut the tether. In some variations, the tether-cutting device may employ a stopper mechanism to prevent the lead screw from turning, a mechanism to prevent the lead screw from coming into contact with the cutting blade, or a mechanism to prevent movement of the cutting blade. In one variation, a stopper mechanism may be used to prevent the lead screw from turning. For example, a safety tab may be inserted through the proximal handle and into a slot in the sidewall of the lead screw such that the lead screw can no longer turn. In another variation, the lead screw may be moveable within the proximal handle such that the operator can control whether the lead screw is in contact with the cutting blade in order to control whether the cutting blade may move. For example, the lead screw may be held in a first position by the proximal handle in which the lead screw is not in contact with the cutting blade so that the cutting blade cannot be moved. The cutting blade may comprise threading, or may be friction fit within the inner body of the proximal handle, such that it will not move unless the lead screw engages it. The lead screw may be held in position by the proximal handle by any suitable mechanism including friction fit, threading, or a safety tab as described above in relation to preventing the movement of the lead screw. The operator may move the lead screw into a second position in which the lead screw is in contact with the cutting blade to allow the cutting blade to be moved. The operator may move the lead screw from the first position to the second position in any suitable manner. For example, the operator may push or turn the lead screw into place, or may remove a safety tab, in order to move the lead screw into contact with the cutting blade. In a further variation of the devices described herein, a mechanism may be used to prevent the cutting blade from turning. For example, as described above in relation to the lead screw, the cutting blade may comprise a slot in a sidewall. A safety tab may be inserted through the proximal handle and into the slot to prevent the cutting blade from rotating and/or translating. It should be appreciated that any suitable mechanism may be employed to interfere with the movement of the actuation mechanism, the lead screw, and/or the cutting blade. In some variations, two or more the mechanisms described herein may be combined to prevent movement of the cutting blade.

In one variation, the inner shaft is stationary within the lumen of the catheter. The inner shaft may be held stationary, for example, by coupling the inner shaft to the proximal handle of the tether-cutting device using a friction fit inside the inner body of the proximal handle. The inner shaft may also be held stationary by coupling the inner shaft to the outer shell of the proximal handle. Any suitable mechanism may be used to couple the inner shaft to any surface of the proximal handle including adhesive, soldering, brazing, bonding, fusing, hooks, screws, hinges, frictional or interference fit, collets, flared connection, or grips. Alternatively or additionally, the inner shaft may be moveable within the lumen of the catheter. For example, the inner shaft may be able to move distally and proximally within the lumen of the catheter.

Movement of the inner shaft may be facilitated by an actuation mechanism. The actuation mechanism may be wheel-shaped such that the user facilitates movement of the inner shaft by turning the actuation mechanism. However, the actuation mechanism may comprise any suitable configuration, may have any suitable cross section, and may be moved in any suitable manner, as described above in reference to the actuation mechanism to control the cutting blade. The actuation mechanism need not be moved by rotation, but may instead be moved in any suitable manner, including sliding, pulling, or pushing. For example, the actuation mechanism may be in the form of a flat moveable belt or band, such that the user slides the belt to move the inner shaft. Alternatively, the actuation mechanism may be in the form of a sliding notch, such that the user slides the notch in order to facilitate movement of the inner shaft. The actuation mechanism may also be in the form of a switch or button, such that pushing the switch or button may be used to facilitate the motion of the inner shaft. The actuation mechanism controlling the movement of the inner shaft within the lumen of the catheter may be partially contained within the proximal handle of the tether-cutting device. The inner shaft actuation mechanism may protrude through an opening in the outer shell of the inner shaft so that the operator may engage the actuation mechanism. The actuation mechanism may operate to control the movement of the inner shaft in any suitable manner. For example, the actuation mechanism may be coupled to a lead screw, the rotation of which results in proximal or distal translation of the inner shaft. Any suitable mechanism such as gears, a rack and screw, a rack and pinion, a slider crank mechanism, a cam and roller, a crank and rod, friction wheels, pulleys, or any other suitable mechanism may be employed to actuate the inner shaft. The operation of these mechanisms in relation to movement of the cutting blade, as described above, apply equally to the operation of these mechanisms when employed to facilitate the movement of the inner shaft.

One variation of a tether-cutting device with a moveable inner shaft may also include a safety mechanism to hold the inner shaft stationary within the lumen of the catheter until the operator is ready to move the inner shaft. This mechanism may comprise an inner shaft safety tab coupled to an actuation mechanism, where the safety tab operates to physically interfere with the movement of the actuation mechanism, thereby preventing movement of the inner shaft. For example, the actuation mechanism may comprise a series of protrusions, and the inner shaft safety tab may be inserted into the proximal handle and between two protrusions of the actuation mechanism to prevent the actuation mechanism from being moved. However, any suitable mechanism may be used to prevent movement of the actuation mechanism, including those described above in reference to a safety tab to prevent the cutting blade actuation mechanism from rotating and/or translating the cutting blade.

In some variations of the tether-cutting device described herein, the cutting blade may be simultaneously rotated and translated about the inner shaft to cut the tether. Simultaneous rotation and translation may allow the cutting blade to exert a shearing or slicing force on the tether, such that the cutting blade can effectively cut through strong surgical tethers. However, in other variations of the tether-cutting device, the cutting blade may not be simultaneously rotated and translated. In one example, the device may comprise a blade that may only be translated. In another example, rotation and translation may be controlled by different mechanisms.

In some variations, the cutting blade may be both proximally and distally translated within the catheter lumen with similar or identical friction and tracking force. That is, the operator may be able to move the cutting blade both proximally and distally within the lumen of the catheter with substantially equal effort. The ability to easily advance and withdraw the cutting blade may allow for greater flexibility in the maneuvering of the blade, and may facilitate repositioning of the cutting blade. For example, the operator may advance the catheter, begin to actuate the blade, but subsequently realize that the catheter should be repositioned. The bidirectional translation of the tether-cutting device allows the operator to move the blade proximally within the lumen back to its more-proximal location and reposition the catheter. Further, the ability to both proximally and distally translate the blade gives the operator more than one chance to cut the tether in case of a malfunction. For example, if the blade is not successful in cutting the tether, the operator can reposition the cutting blade and repeat the cutting process.

Figure 3A:
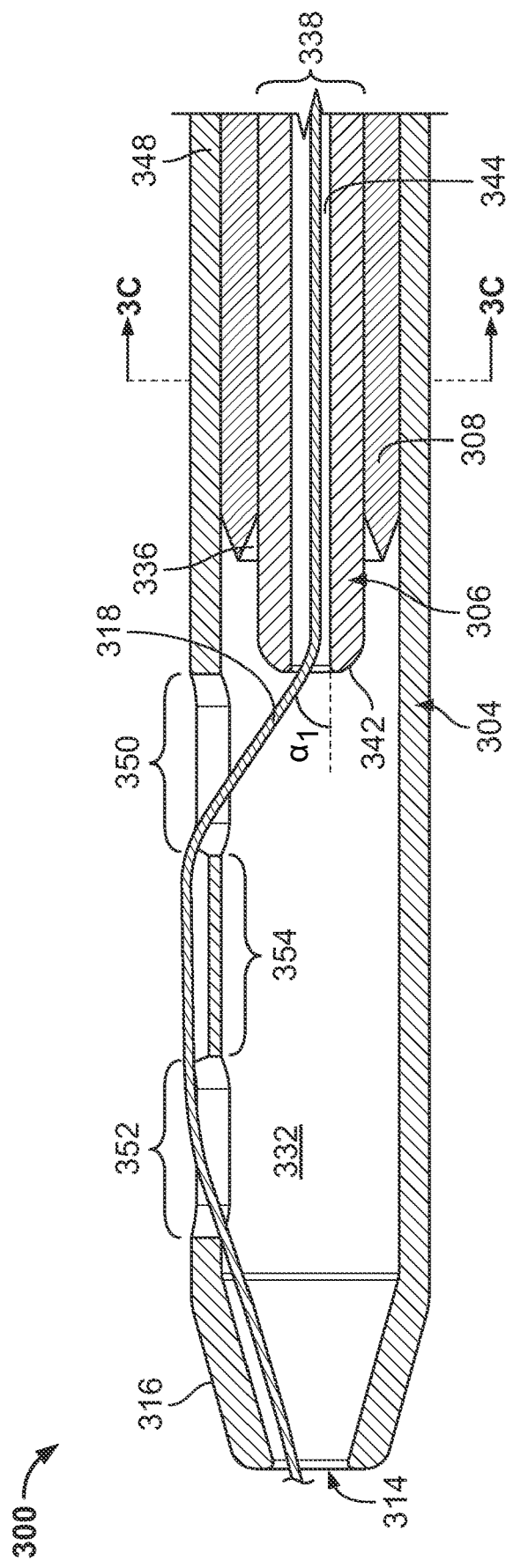
FIGS. 3A and 3B depict schematic side cross-sectional views of a variation of a tether-cutting device.

FIG. 3A shows one exemplary variation of a tether-cutting device (300) that includes a catheter (304), a cutting blade (308), and an inner shaft (306). The catheter comprises a proximal end, a distal end (316), a lumen (332) that extends between the proximal and distal ends, and a distal opening (314). A distal portion of the catheter (304) may be tapered toward the distal opening (314). The cutting blade (336) comprises a proximal end (not pictured in FIG. 3A), a distal end (336), and a lumen (338) that extends between the proximal and distal ends. The inner shaft comprises a proximal end (not pictured in FIG. 3A), a distal end (342), and lumen (344) that extends between the proximal and distal ends. The inner shaft (306) and the cutting blade (308) are coaxially disposed within the catheter lumen (332). In this variation, the inner shaft (306) is disposed within the cutting blade lumen (338). This concentric arrangement is further depicted in FIG. 3C, which is a cross-sectional view taken at line 3C-3C in FIG. 3A. FIG. 3C depicts the inner shaft (306) disposed within the cutting blade (308), and the cutting blade (308) disposed within the catheter (304). The cutting blade (308) may be moveable about the inner shaft (306) within the lumen (332) of the catheter. The sidewall (348) of the catheter of FIG. 3A comprises first (350) and second openings (352). The second opening (352) is distal to the first opening (350). In FIG. 3A, the first opening (350) and the second opening (352) are circumferentially aligned along the sidewall (348) of the catheter, with a length of the catheter (354) spaced between them. However, in some variations of the tether-cutting device described herein, the first and second openings may not be circumferentially aligned and may instead be offset from each other so that each opening is at a different circumferential location on the catheter. Further, the length of catheter (354) between the openings may be of any suitable length. A tether (318) may be threaded into the lumen (332) of the catheter (304) through the distal opening (314), out of the lumen (332) of the catheter (304) through the second opening (352), and back into the lumen (332) of the catheter (304) through the first opening (350). The tether (318) may then be extended from the first opening (350) into the lumen (344) of the inner shaft (306) such that the tether (318) extends across a portion of the catheter lumen (332) at an angle ($\alpha_1$) which is shallow enough to facilitate low tracking force when advancing the cutting device to, or withdrawing from, the target site.

As shown in FIG. 3A, the cutting blade (308) may have a first position, in which the distal end (336) of the cutting blade (308) is proximal to the distal end (342) of the inner shaft (306). When the cutting blade (308) is in the first position as depicted in FIG. 3A, the inner shaft (306) may protect the tether (318) from being cut by the cutting blade (308) by retaining the tether distal to the cutting blade. When the cutting blade (308) is proximal to the inner shaft (306), the tether (318) cannot be cut by the cutting blade (308). This arrangement may help to protect the tether (318) from being prematurely cut when the cutting blade (318) is held in the first position.

Figure 3B:
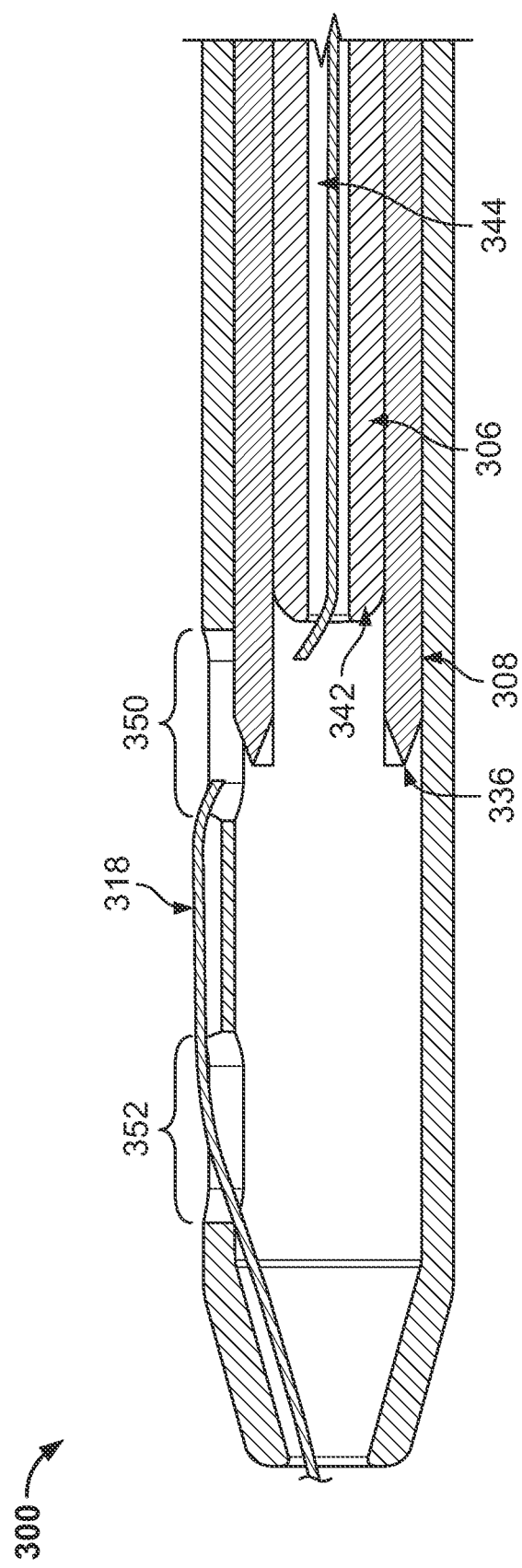

FIG. 3B shows a variation of the tether-cutting device (300) in which the cutting blade (308) has been moved from the first position described in FIG. 3A to a second position shown in FIG. 3B. In FIG. 3A, the distal end (336) of the cutting blade (308) is proximal to the distal end (342) of the inner shaft (306). In FIG. 3B, however, the distal end (336) of the cutting blade (108) has been advanced past the distal end (342) of the inner shaft (306) to cut the tether such that the distal end (336) of the cutting blade is distal to the distal end (342) of the inner shaft. The tether (318), when extended between the first opening (350) and the lumen (344) of the inner shaft (306), forms a path that is traversed by the cutting blade (308) as the cutting blade (308) moves from the first position to the second position. In one variation of this device, the cutting blade (308) is simultaneously rotated and translated about the inner shaft as it moves from the first to second position. The simultaneous rotation and translation may create a shearing or slicing effect to effectively cut through the tether. Tethers used in surgical settings must be strong enough to hold pieces of tissue together, and therefore may be very difficult to cut. The slicing motion of the cutting blade (308) created by simultaneous rotation and translation may provide the benefit of allowing the cutting blade (308) cut through very strong material.

Devices and methods described herein may also provide the benefit of preventing the formation of loose pieces of tether after the tether has been cut. As described above and depicted in FIG. 3A, the tether is extended across only the portion of the catheter lumen (332) between the first opening (350) and the inner shaft (306). Therefore, when the cutting blade (308) moves from the first position to the second position, the cutting blade (308) only cuts the tether (318) at one point along the length of the tether. This may provide the advantage of preventing the formation of loose pieces of tether. If the tether were, for example, fully extended across the lumen of the catheter, the cutting blade may come into contact with the tether at more than one point. This may result in the formation of a piece of tether that is not attached to either the target site or the proximal end of the tether. Loose pieces of tether are problematic because they may exit the catheter and move into the body of the subject.

Devices and methods described herein may also provide the benefit of preventing the tether from escaping the path of the cutting blade. In the arrangement depicted in FIGS. 3A and 3B, a tether may be extended from the first opening (350) in the catheter and into to the lumen (344) of the inner shaft. When the cutting blade (308) is moved distally within the catheter lumen along the inner shaft (306), it traverses the path of the tether (318) extended between the first opening (350) and the inner shaft lumen (344). In this arrangement, even if the tether (318) were to become slack, the cutting blade (308) will come into contact with the tether (318) as the cutting blade (308) is moved distally. Thus, the variation depicted in FIGS. 3A and 3B prevents the tether (318) from being able to escape the path of the cutting blade (308).

In some variations, the inner shaft may be kept stationary within the lumen of the catheter. This may help simplify the operation and/or manufacturing of the device, reduce operator error, and/or reduce the amount of time required to operate this device. Further, it may result in less risk of a malfunction of the device related to unintended movement of the inner shaft. In other variations, the inner shaft may be movable within the lumen of the catheter. Proximal and distal movement of the inner shaft may allow the operator to adjust the angle $\alpha_1$ (as shown in FIG. 3A) of the tether when it extends between the first opening of the catheter and the lumen of the inner shaft. This ability to move the inner shaft may provide the benefit of allowing the operator to adjust the tracking force of the tether and/or facilitate cutting the tether.

The inner shaft may have a predetermined range of motion within the lumen of the catheter where the inner shaft is able to move proximally and distally within the range. The tether-cutting device may have a retracted configuration in which the inner shaft is moved proximally within the catheter lumen, and an extended configuration in which the inner shaft is moved distally within the catheter lumen. When the inner shaft is moved proximally into the retracted configuration, the angle between the tether and the lumen of the inner shaft ($\alpha_1$ in FIG. 3A, for example), may be reduced. A reduction in $\alpha_1$ may help to reduce the amount of force that is used to advance the tether-cutting device (e.g., the tracking force) over the tether. Reduced tracking force may facilitate the advancement of the catheter assembly over the tether. When the inner shaft is moved distally into the extended configuration the angle $\alpha_1$ is increased. An increase in $\alpha_1$ may increase the portion of the tether that crosses the path of the cutting blade, which may facilitate the cutting of the tether. Increasing $\alpha_1$ may also increase the tracking force such that the tether-cutting device is less likely to slip while the operator is in the process of advancing the cutting blade to contact and cut the tether.

Figure 4A:
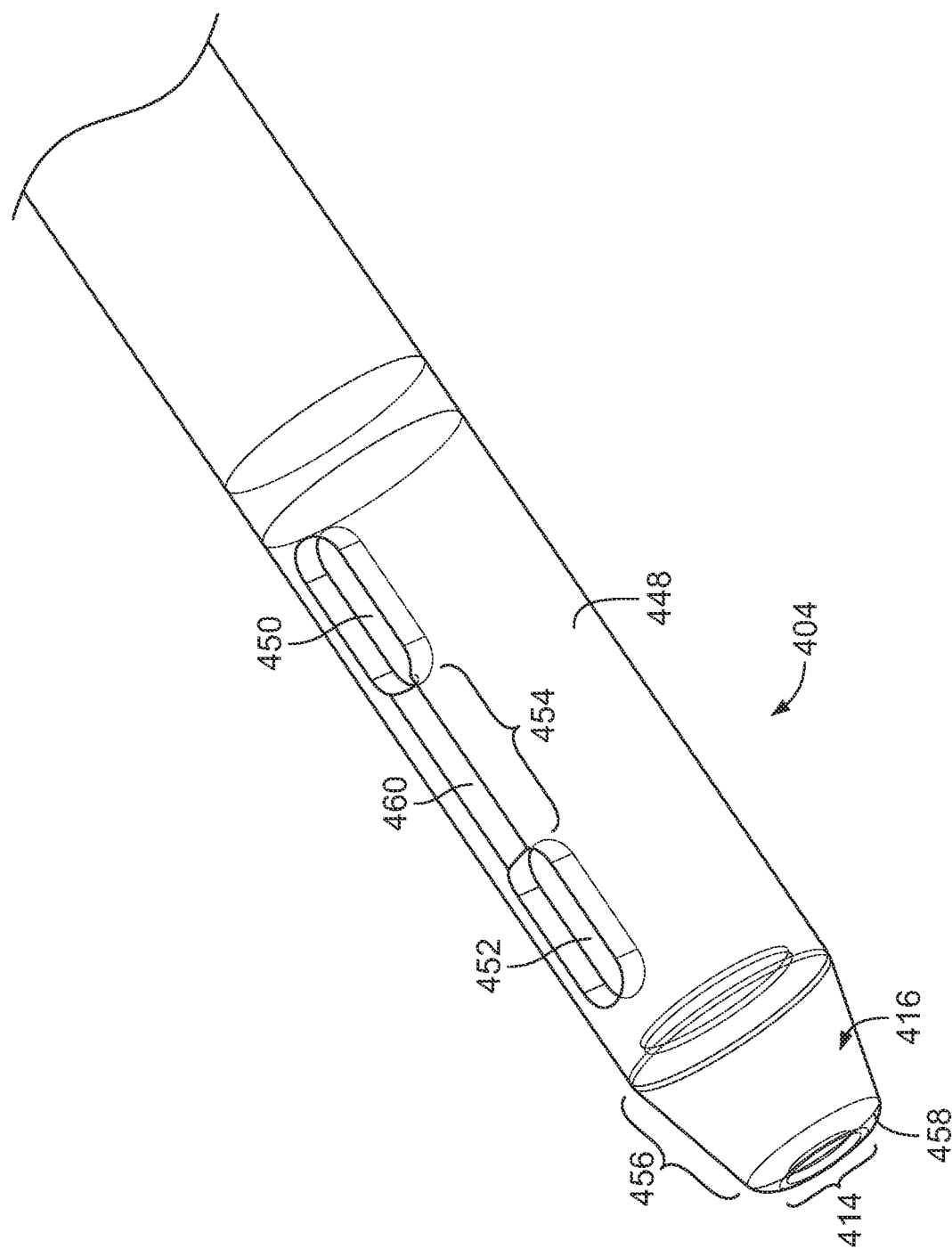
FIGS. 4A-4C depict perspective views of the components of one variation of a tether-cutting device.

FIG. 4A depicts an exemplary variation of a distal portion of a catheter (404) of a tether-cutting device. As depicted in FIG. 4A, the catheter (404) may be substantially cylindrical in shape. However, in other variations, the catheter may be any suitable shape. For example, the catheter may have a square-shaped, rectangular, ovular, or triangular cross-section. The catheter may comprise an opening (414) at the distal end (416). This opening may be configured to receive a tether. The catheter may have a distal tip portion (456) at the distal end (416). In some variations, the distal tip portion (456) may be tapered or have a substantially conical profile. That is, in the tip portion, the circumference of the catheter may narrow as it reaches the distal opening (414). The distal end (416) of the catheter (404) may have an atraumatic rounded edge (458). A rounded edge may prevent the catheter (404) from damaging an outer catheter through which the cutting catheter is advanced and/or the patient as the catheter (404) is advanced to the target site. Further, a rounded edge may prevent the catheter (404) from partially or fully cutting the tether (418) in an undesired location, or at an undesirable point in time.

As stated above, the catheter may comprise one or more openings in the sidewall (448) of the catheter. For example, the catheter (404) may have a first opening (450) and a second opening (452), as depicted in FIG. 4A. The openings may be configured to receive a tether. The openings may be of any suitable shape, such as oval, round, rectangle, or square shaped. The openings may also be of any suitable size to allow a tether to pass through. The openings may also have rounded or smoothed edges. Rounded or smoothed edges may provide the benefit of preventing the opening from cutting or damaging the tether such as, for example, during the threading of the tether, and/or as the tether is tensioned, and/or as the catheter is advanced over the tether to the cut location. The openings may be aligned with respect to each other in any suitable manner. For example, the openings may be circumferentially aligned, as depicted in FIG. 4A. However, the openings may have any suitable alignment. The space between the openings (454) may be of any suitable distance. The space between the openings may comprise a groove or depression (460) as shown in FIG. 4A. The depression (460) may be of sufficient width to contain the tether. This depression (460) may provide the benefit of directing the path of the tether as it is extended between the second opening (452) and the first opening (450). The depression (460) may be of any suitable depth or width to house a tether. An additional benefit of a depression (460) between the openings in the sidewall (448) of the catheter (404) is that it may help to keep the tether in place and in tension as the cutting blade (408) is advanced to cut the tether. For example, the depression may prevent the tether from moving laterally as the cutting blade comes into contact with the tether (e.g. the rotation of the cutting blade may push the tether in a lateral direction, and the depression may help keep the tether stationary). Holding the tether in place may facilitate the cutting of the tether. Alternatively or additionally, the catheter may comprise a tether lumen between the first and second openings, where the lumen may partially or completely enclose a tether extending between the first and second openings. In some variations, the lumen may be located within the thickness of the sidewall of the catheter. Alternatively, the catheter may not comprise a groove or depression between the first and second openings.

The catheter may be made of any suitable material such as polymer, plastic, metal, impregnated textile or cloth, natural or synthetic rubber, natural or synthetic fibers (including woven and/or braided fibers). The catheter may be flexible, so as to facilitate easy movement of the catheter through the subject. The catheter need not have a uniform material in all portions of the catheter. For example, the catheter may be made of plastic at some locations, and metal at others.

Figure 4B:
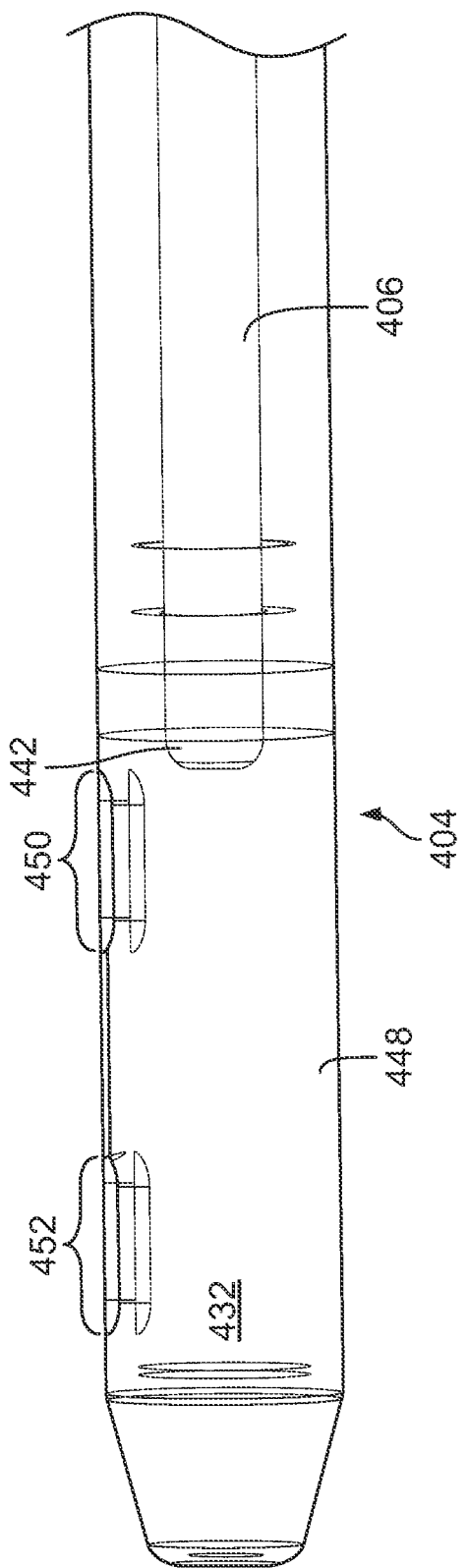

FIG. 4B depicts the inner shaft (406) situated within the lumen (432) of the catheter (404). In FIG. 4B, the distal end (442) of the inner shaft (406) is proximal to the first opening (450) in the sidewall (448) of the catheter. However, it should be appreciated that the distal end (442) of the inner shaft (406) could be situated at any point within the lumen (432) of the catheter. For example, the distal end (442) of the inner shaft (406) may be aligned with any point along the length of the first opening (450), or the distal end (436) of the inner shaft (406) could be distal to the first opening (450). For example, the distal end of the inner shaft (406) could be situated between the first opening (450) and the second opening (452). Further, the distal end (442) of the inner shaft (406) could be aligned with, or positioned distal to, the second opening (452). FIG. 4B shows the inner shaft (406) as having a circular cross section, but it should be appreciated that the inner shaft (406) can be any suitable shape. For example, the inner shaft may have a square-shaped, rectangular, triangular, or ovular cross section. Further, the inner shaft (406) can be made of any suitable material. The inner shaft (406) may be flexible, or it may be rigid. Further, as stated above, the inner shaft (406) may be held stationary within the lumen (432) of the catheter (404), or it may be moveable. For example, the inner shaft (406) may be able to be moved proximally and distally within the lumen (432) of the catheter, as described above. The distal end (442) of the inner shaft (406) may be blunted or rounded. An advantage of an inner shaft (406) with a blunted or rounded distal end is that it may prevent damage to or unintended cutting of the tether. A rounded or blunted distal end (442) of the inner shaft (406) may protect the tether from being cut at an undesired location, or at an undesired point in time.

As described above, the inner shaft (406) may comprise a lumen. The lumen of the inner shaft (406) may be configured to house a tether. The inner shaft lumen may have any suitable diameter. For example, the diameter of the inner shaft lumen may track closely with the width of a tether, such that there is very little excess space when a tether is housed within the lumen of the inner shaft (406). However, the diameter of the inner shaft lumen may also be much larger than the width of a tether. The inner shaft (406) may be held within the lumen (432) of the catheter in any suitable manner. The inner shaft (406) may also be connected to the proximal handle in any suitable manner. For example, the inner shaft (406) may be molded to a surface of the proximal handle. In another variation, the inner shaft (406) may be held in place within the hollow inner body of the proximal handle by frictional forces. For example, the inner shaft may be held within the inner body of the proximal handle by friction fitting a proximal portion of the inner shaft (406) housed within the inner body to an inner surface of the proximal handle.

Figure 4C:
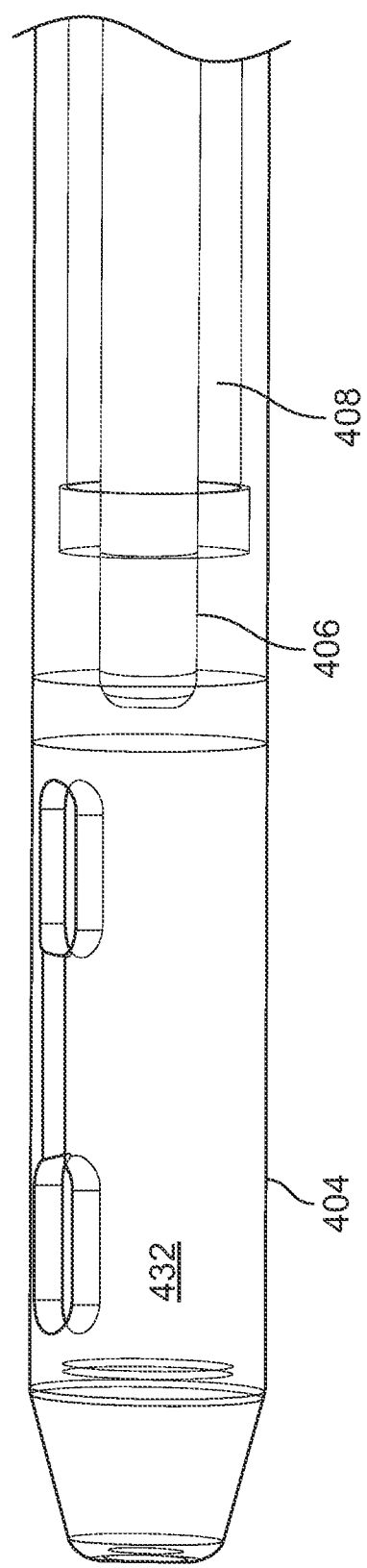

FIG. 4C depicts the cutting blade (408) situated within the lumen (432) of the catheter (404), and disposed over the inner shaft (406). As described above, the cutting blade (408) may be movably disposed about the inner shaft (406) in any suitable manner. For example, the cutting blade (408) may be able to be rotated and moved distally and proximally about the inner shaft (406) within the lumen (432) of the catheter (404). The distal end of the cutting blade (408) may have a sharpened edge, suitable for cutting a tether. The cutting blade may comprise a distal portion with a sharpened edge, and a proximal portion with a flexible shaft. The cutting blade (408) may be made of any suitable material. For example, the cutting blade may be made of stainless steel, metal, liquid crystal polymer, natural or synthetic gems, or ceramic. In some variations, the cutting blade may be made of heated materials such as nichrome, and/or any conductive material and heated with electrical energy. A cutting blade comprised of any of the listed materials may be also combined with energy output such as radiofrequency (RF), vibratory energy, or laser-based energy to facilitate cutting the tether. The cutting blade may also be made of one or more materials. For example, the sharpened edge of the cutting blade may be made of metal, whereas the body of the cutting blade may be made of plastic, and/or braided or woven polymers and/or metallic alloys. In some variations, the cutting blade may comprise a distal portion made of a rigid material such as metal, and a proximal portion made of a flexible material such as flexible plastic or rubber. For example, in some variations, the cutting blade may comprise a sharpened distal end made of metal, and a flexible shaft made of a flexible plastic. The cutting blade (408), as depicted in FIG. 4C has a circular cross section, but the cutting blade may be of any suitable shape. For example, the cutting blade may have an ovular, square-shaped, rectangular, or triangular cross section.

In devices described herein, the cutting blade may be moveable to any suitable distance within the lumen of the catheter. For example, it may be possible to move the cutting blade along the entire length of the catheter. However, it may also be the case that it is only possible to move the cutting blade a certain distance within the lumen of the catheter. For example, a lead screw in the proximal handle that controls the movement of the cutting blade may only have sufficient threading to move the cutting blade a certain distance within the length of the catheter. It may also be the case that the lead screw engages with threading on the cutting blade, and the cutting blade may only have sufficient threading to move a certain distance along the length of the catheter. In another variation, there may a mechanism to prevent the cutting blade from moving past a certain point within the lumen of the catheter. Any suitable mechanism can be used to prevent the cutting blade from moving. For example, the cutting blade may comprise a notch on an outer surface, and the catheter may comprise a slot on an inner surface of the catheter sidewall configured to house or otherwise engage with the notch. The slot may be a full opening in the sidewall of the catheter, or it may be a groove or depression/recess the catheter sidewall. The notch on the cutting blade and the slot in the catheter may be arranged such that the notch cannot move out of the slot, but can slide along it. Therefore, the length of the slot may correspond to the distance the cutting blade can be moved within the lumen of the catheter. In another variation, the catheter may comprise a notch, and the cutting blade may comprise a slot that functions as described above to restrict the movement of the cutting blade. In another variation, the catheter may comprise a protrusion on an interior surface of the sidewall. The protrusion may extend into the lumen of the catheter such that when the distal end of the cutting blade comes into contact with the protrusion it can no longer advance within the lumen of the catheter. The protrusion may be at any suitable location along the length of the catheter, such as at or near the distal end. In another variation, the distal tip of the catheter may be tapered such that the cutting blade can no longer fit through the catheter lumen due to the reduction in the diameter of the catheter. Thus, the cutting blade is prevented from moving beyond the point of the catheter lumen at which the diameter of the catheter is equal to or less than the diameter of the cutting blade. One advantage of providing a mechanism to stop the cutting blade is that limiting the movement of the blade may prevent the blade from damaging portions of the tether-cutting device. For example, if the blade were able to move along the entire length of the lumen of the catheter, it may come into contact with and damage the sidewall of the catheter.

Figure 5A:
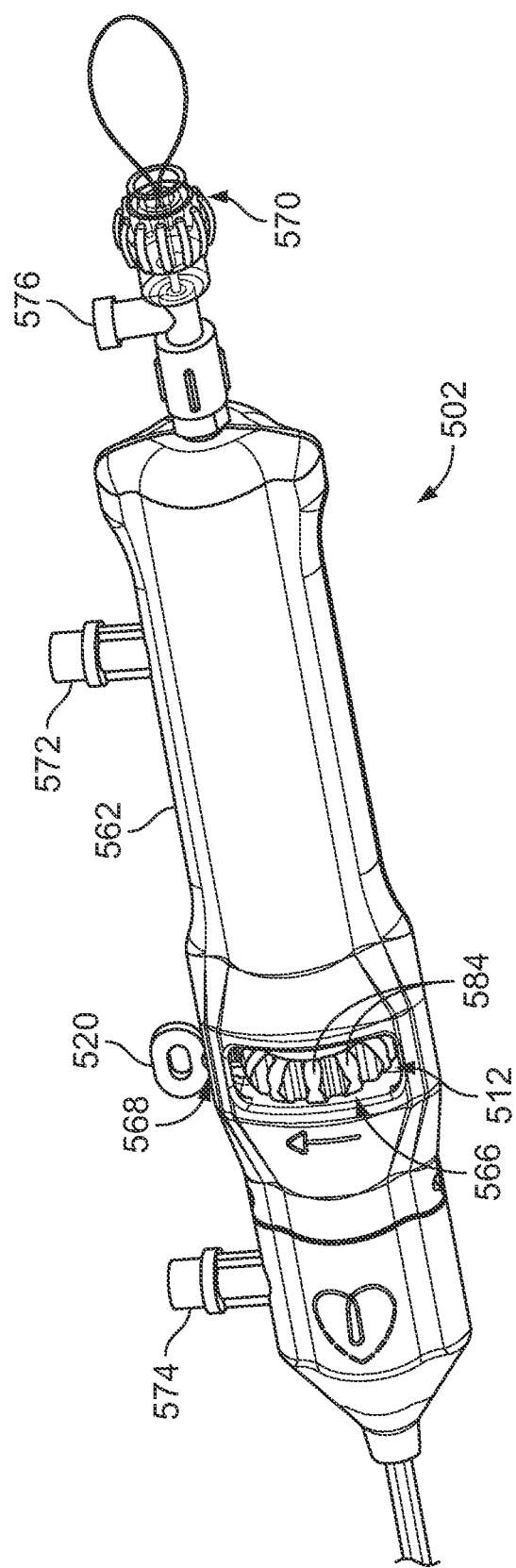
FIG. 5A depicts a perspective view of a proximal handle of a tether-cutting device.

As shown in FIG. 5A, the tether-cutting device may comprise a proximal handle (502). The proximal handle (502) may allow the operator to control the operation of the tether-cutting device, and control the movement of the various components, such as the cutting blade and/or the inner shaft, for example. The proximal handle (502) may comprise an outer shell (562), defining a substantially hollow inner body. The outer shell (562) may comprise one or more openings to accommodate various components, such as buttons, dials, wheels, ports and/or structures that may be used to control operation of the device. For example, the outer shell (562) may comprise an opening (566) configured to house an actuation mechanism (512) such that the operator can control the actuation mechanism (512) while gripping the proximal handle (502). In the variation of FIG. 5A, the actuation mechanism (512) may comprise a rotatable disc (e.g., a wheel-shaped element or dial) having a series of protrusions (584) disposed about the outer circumference of the disc. The wheel-shaped actuation mechanism (512) depicted in the variation of FIG. 5A may be turned by the operator to facilitate movement of the cutting blade. As described above, the actuation mechanism may comprise any suitable configuration, such as any suitable mechanism described herein.

The proximal handle may also house a safety tab (520), removably coupled to the actuation mechanism (512). FIG. 5A depicts a safety tab (520) inserted into an opening (568) in the proximal handle (502). The safety tab opening (568) in the proximal handle (502) may allow the safety tab (520) to come into contact with the actuation mechanism (512), in order to prevent the actuation mechanism (512) from moving until the safety tab (520) is removed. The proximal handle (502) may also comprise various ports to allow to entry and exit of various objects through the catheter, inner shaft, or cutting blade. For example, the proximal handle (502) may comprise a tether port (570) at the distal end to allow the tether to exit through the proximal handle. A tether port (570) to allow the tether to exit the proximal handle (502) may allow the tether to be held in tension outside of the device. For example, one or more weights may be attached to the proximal portion (e.g., proximal end) of the tether that extends out of the tether port (570) in order to place the tether in tension. Various mechanisms may be used to hold the proximal portion of the tether in tension. For example, the operator may simply hold the tether in tension as the tether is being cut. The tether-cutting device may also possess mechanisms to hold the tether in tension, such as hooks, grips, pulleys, or any suitable mechanism to hold a tether in tension.

The proximal handle (502) may also include various flush ports that allow the operator to introduce fluids into various components of the device. For example, the outer flush port (572) may be in fluid communication with the catheter lumen in order to allow the operator to flush liquid through the catheter. The inner flush port (574) may be in fluid communication with the inner shaft lumen in order to allow the operator to flush liquid through the inner shaft. The cutter flush port (576) may be in fluid communication with the cutting blade lumen in order to allow the operator to flush liquid through the cutting blade. Various flush ports may allow entry or exit of liquids into or out of the device. As described above, any of the ports herein may also allow for entry and exit of various devices and/or substances into the tether-cutting device.

Figure 5B:
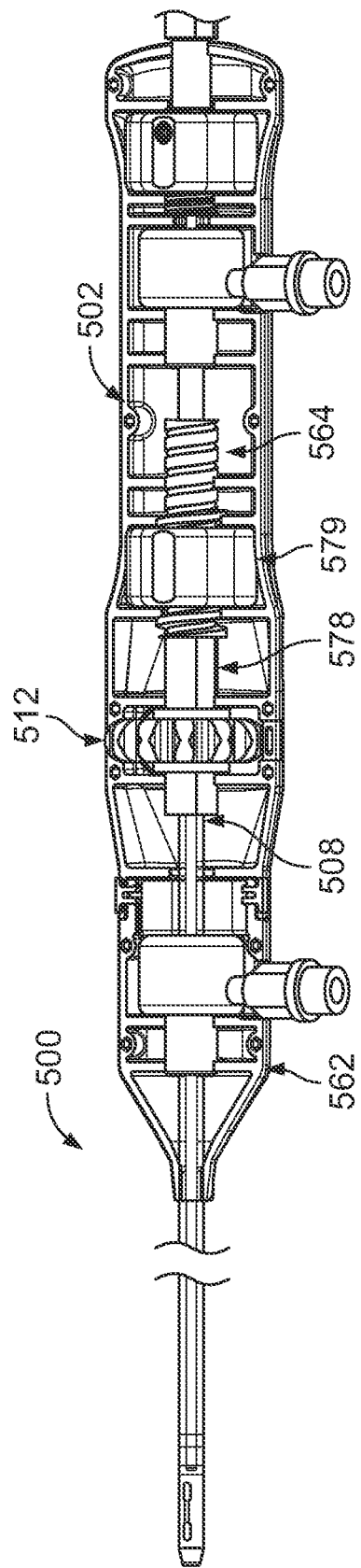
FIGS. 5B and 5C depict side partial cutaway views of the components of one variation of a tether-cutting device.
Figure 5C:
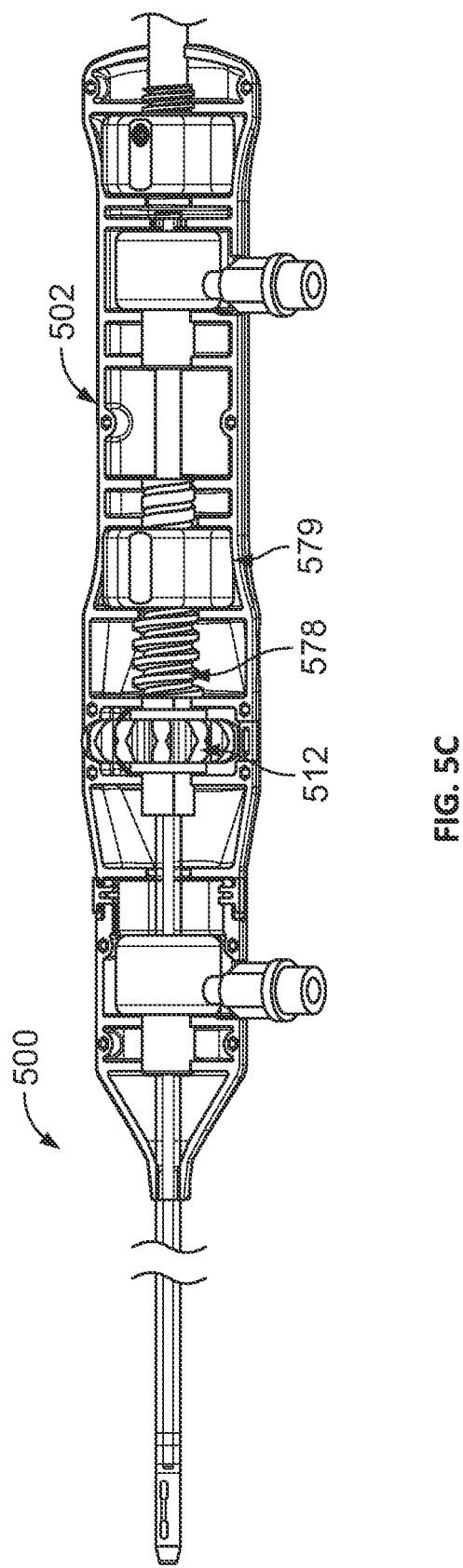

FIGS. 5B and 5C are side partial cutaway views of a tether-cutting device (500) showing examples of various mechanisms that may be used to control the movement of the cutting blade. As shown in FIG. 5B, an actuation mechanism (512) in the proximal handle (502) of the tether-cutting device (500) may be coupled to a lead screw (578) housed within the inner body (564) of the proximal handle (502). The lead screw may be coupled to the cutting blade, such that movement of the lead screw facilitates movement of the cutting blade. The lead screw may be coupled to the cutting blade in any suitable manner, such as by friction fit of the cutting blade within an opening of the lead screw, fixedly attaching the proximal end of the cutting blade to the distal end of the lead screw (e.g. using an adhesive, soldering, or molding), or any other attachment mechanism. In the variation of FIGS. 5B and 5C, the lead screw (578) is coupled to the cutting blade (508) such that rotation of the lead screw translates into rotation and proximal or distal (depending on the direction the screw is turned) movement (e.g., longitudinal translation) of the cutting blade (508) within the lumen of the catheter.

In FIGS. 5B and 5C, the lead screw (578) rotates when the user turns the actuation mechanism (512) because the actuation mechanism is coupled to the lead screw via friction fit of the lead screw (578) within an opening of the actuation mechanism (512). As described below, the opening of the actuation mechanism may be configured to conform to one or more surfaces of the lead screw to facilitate movement of the lead screw upon turning the actuation mechanism. The lead screw may interact with a nut in the proximal handle to facilitate the longitudinal movement of the lead screw. For example, as shown in FIGS. 5B and 5C, the lead screw (512) is extended through a nut (579), such that when the actuation mechanism rotates the lead screw, threading on the lead screw engages with an interior surface of the nut to move the lead screw proximally or distally (depending on the direction of turning) within the proximal handle. The nut may comprise threading on an interior surface that engages with threading on the lead screw, such that turning of the lead screw causes the threading of the nut to engage with the threading of the lead screw to translate the lead screw distally or proximally. Thus, when the user turns the actuation mechanism (512), the lead screw (578) moves from a first position, as depicted in FIG. 5B, to the second position, as depicted in FIG. 5C. The nut and lead screw combination may facilitate longitudinal movement of the cutting blade in any suitable manner.

Figure 5E:
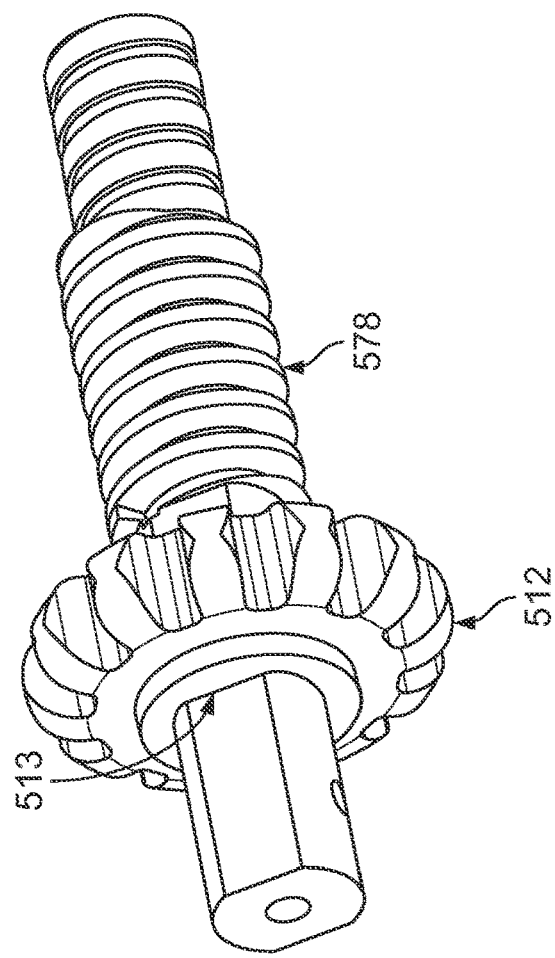
FIGS. 5D-5G depict perspective views of the components of one variation of a tether-cutting device.
Figure 5D:
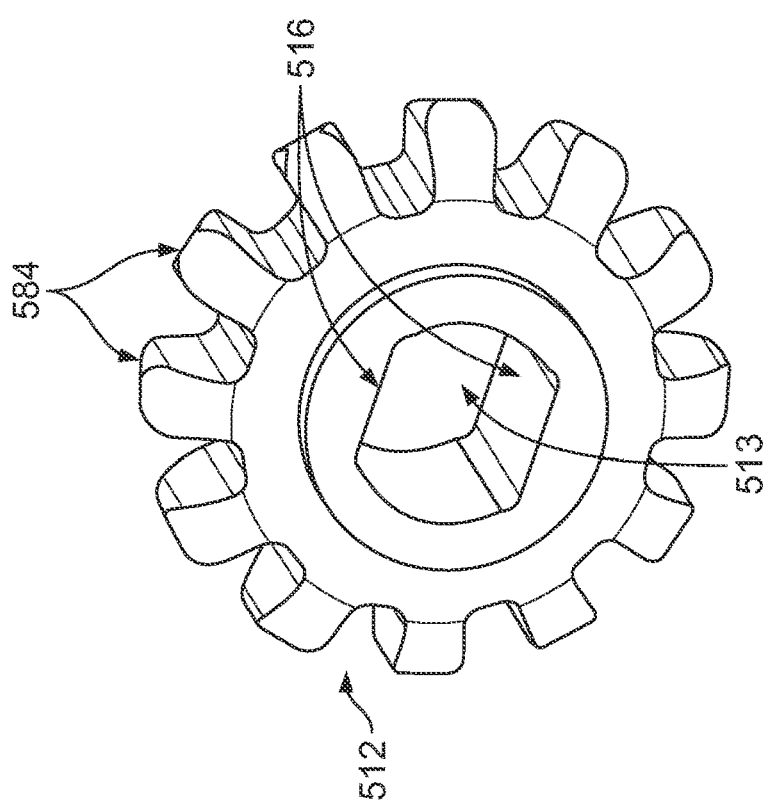

FIGS. 5D and 5E show exemplary variations of the actuation mechanism (512), and lead screw (578) coupled to the actuation mechanism (512). As depicted in FIG. 5D, the actuation mechanism comprises protrusions (584) and an opening (513), which may be configured to engage with the lead screw (578). That is, the opening (513) of the actuation mechanism (512) may be configured to fit the dimensions of the outer surface of the lead screw (578). For example, the actuation mechanism depicted in FIG. 5D comprises two flattened surfaces (516) and two curved surfaces, configured to mirror the surfaces of the lead screw. This may provide the benefit of improving the engagement of the actuation mechanism (512) with the lead screw (578). However, the opening of the actuation mechanism may be configured in any suitable manner with any combination of curved or flat surfaces. As shown in FIG. 5E, the lead screw (578) may extend through the opening (513) of the actuation mechanism (512). In FIG. 5E, the actuation mechanism (512) is friction fit to the lead screw (578), such that when the actuation mechanism rotates, it also rotates the lead screw. The lead screw (578) in FIG. 5E comprises two flattened surfaces configured to fit the two flattened surfaces of the actuation mechanism (512). However, the lead screw may comprise any suitable configuration suitable to fit within an opening of the actuation mechanism. The actuation mechanism may be coupled to the lead screw in any suitable manner. For example, in some embodiments, the lead screw may not extend through an opening in the actuation mechanism. Rather, protrusions on the actuation mechanism may interact with threading or protrusions on the surface of the lead screw such that when the actuation mechanism is rotated or moved the protrusions on the actuation mechanism engage with the threading/protrusions on the lead screw. In another variation, the actuation mechanism may be in physical contact with a surface of the lead screw such that frictional forces allow movement of the actuation mechanism to affect movement of the lead screw.

Figure 5G:
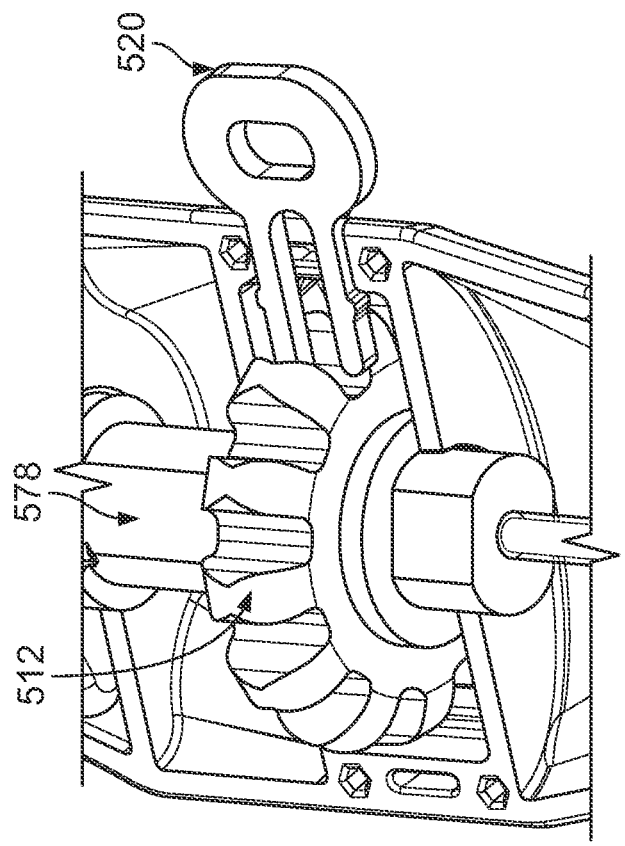
Figure 5F:
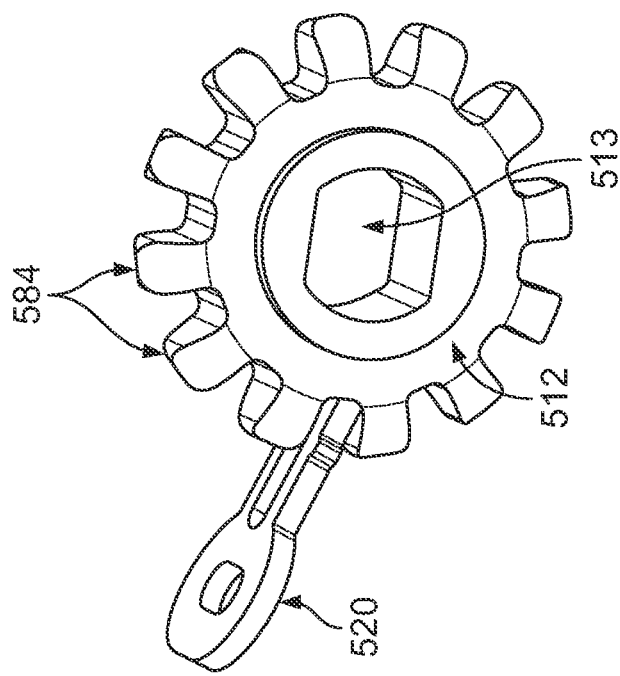

As described above, mechanisms (e.g. safety tabs) may be used to maintain the cutting blade in a stationary position within the lumen of the catheter until the operator is ready to cut the catheter. FIGS. 5F and 5G depict two views of a variation of a safety tab (520) that may be used to prevent the actuation mechanism (512) from turning, thereby preventing the cutting blade from moving within the lumen of the catheter. In the arrangement shown in FIGS. 5A, 5F, and 5G, the safety tab (520) may be inserted into an opening (568) in the proximal handle and between two of the protrusions (584) of the actuation mechanism. When inserted between two of the protrusions (584), the safety tab (520) physically interferes with the rotation of the actuation mechanism. In this arrangement, the operator may remove the safety tab (520) from the opening (568) in the proximal handle (502) to allow movement of the cutting blade.

It should be appreciated that any suitable mechanism can be used to prevent the actuation mechanism from being moved. For example, the safety tab could comprise a small cylindrical or rectangular pin that fits into an opening in the actuation mechanism and the proximal handle. Inserting the pin-like safety tab through the proximal handle and into the actuation mechanism may prevent the actuation mechanism from turning. Further, any suitable mechanism can be used to hold the cutting blade in place in the lumen of the catheter until the operator is ready to move the blade to cut the tether. Alternatively or additionally, a tether-cutting device may have a stopper mechanism to prevent the lead screw from turning, a mechanism to prevent the lead screw from coming into contact with the cutting blade, and/or a mechanism to prevent movement of the cutting blade. In one variation, a stopper mechanism may be used to oppose rotational motion of the lead screw. For example, a safety tab or pin may be inserted through the proximal handle and into a slot in the sidewall of the lead screw such that the tab/pin interferes with the rotation of the lead screw.

In another variation, the lead screw may be moveable within the proximal handle such that the lead screw has a first position in which the lead screw is not in contact with the cutting blade, and a second position in which the lead screw is in contact with the cutting blade. In the first position, the lead screw cannot move the cutting blade because the lead screw and the cutting blade are not in contact. The cutting blade may comprise threading, or may be friction fit within the inner body of the proximal handle, such that it will not move unless it is engaged by the lead screw. The lead screw may be held in the first position by the proximal handle may any suitable mechanism, including friction fit, threading, or a safety tab as described above in relation to preventing the movement of the lead screw. In the second position, the cutting blade may be moved when the lead screw is moved because the cutting blade and the lead screw are in contact. The operator may move the lead screw into contact with the cutting blade in any suitable manner. For example, the operator may push or turn the lead screw into place, or may remove a safety tab in order to move the lead screw into contact with the cutting blade. In some variations, a mechanism may be used to prevent the cutting blade from turning. For example, as described above in relation to the lead screw, the cutting blade may comprise a slot in a sidewall. A safety tab may be inserted through the proximal handle and into the slot to prevent the cutting blade from rotating and/or translating. It should be appreciated that any suitable mechanism can be employed to interfere with the movement of the actuation mechanism, the lead screw, and/or the cutting blade. Further, the mechanisms described herein to prevent movement of the cutting blade may be used alone or in combination.

Methods

Also described herein are variations of methods for cutting a tether. FIG. 6 is a flowchart representation of one variation of a method for cutting a tether. The method (600) may comprise advancing (602) a tether-cutting device over a tether, applying tension to the tether (604), and simultaneously rotating and distally translating (606) the cutting blade in order to the cut the tether. Generally, the operator of a tether-cutting device may advance the catheter assembly, comprising a catheter, an inner shaft, and a cutting blade, over a tether. In some variations, the operator may apply tension to the tether while advancing the catheter assembly over the tether (in addition to applying tension while rotating and translating the cutting blade to cut the tether). Tension may be applied to the tether in any suitable manner, such as those described below. The tether may be connected to a target site in the body of a subject (e.g. as part of an implantable device). In some variations, advancing the catheter over a tether may comprise loading the tether into the tether-cutting device. A loading tool (e.g., a lasso) may be used by the operator to facilitate loading the tether into the device. The loading tool may comprise a loop at one end where the tether can be threaded through. The tool may be then be pulled through the lumen of the catheter(s) to thread the tether through the tether-cutting device. Loading the tether may first comprise threading the tether into the catheter lumen through a distal opening of the catheter, and out of the catheter lumen through a second opening in a sidewall of the catheter. Loading the tether through the device may then comprise threading the tether from the second opening in the sidewall of the catheter, back into the lumen of the catheter through a first, more proximal opening in the catheter. Loading the tether may next comprise threading the tether from the first opening, and through the lumen of the inner shaft. This loading step may result in a portion of the tether extending partially across the lumen of the catheter, from the first opening in the catheter sidewall to the lumen of the inner shaft. The tether may be threaded through the inner shaft, into the proximal handle, and out of the proximal handle through a tether port.

After the tether is loaded into the device, the operator may apply tension to the tether. One advantage to a method that includes applying tension to a tether is that a tether in tension is easier to cut than a tether that is slack. The operator may apply tension to the tether in any suitable manner. For example, the operator may attach weights to the proximal end of the tether to apply tension to the tether. In some variations, the operator may drape the portion of the tether that is proximal to the catheter assembly over a sterile bar. One or more weights may be clamped onto the proximal end of the tether to apply tension. Any suitable weight may be used to apply tension to the tether. For example, a weighted hemostat (or other surgical tool) may be clamped onto the tether. In another variation of the method described herein, the operator may simply hold the tether in tension. In a further variation of the method described herein, the operator may pull the tether into tension and attach the tether to a mechanism of the tether-cutting device, such as a hook, slot, notch, or any other suitable mechanism in order to maintain the tether in tension. The operator may also utilize mechanisms of the tether-cutting device designed to apply tension to the tether, such as pulleys, wheels, spools, or hooks, or any other suitable mechanism, in order to apply tension to the tether.

The operator may advance the catheter along the tether at any suitable point during the operation of the device. For example, the operator may complete all of the threading steps to load the tether into the device, and then advance the catheter to the target site. In another variation, the operator may only complete a subset of the threading steps to load the tether, and then partially advance the catheter along the tether in order to complete the loading of the tether into the device. For example, the operator may thread the tether into the catheter lumen through the distal opening, thread the tether out of the catheter lumen through the second opening in the sidewall of the catheter, and then partially advance the catheter along the tether before threading the tether through the rest of the tether-cutting device. In a further variation, the operator may complete the loading of the tether, advance the tether-cutting device to the target site, partially actuate the blade of the tether-cutting device, and subsequently further advance the tether-cutting device along the tether. For example, the operator may begin to actuate the blade, and realize that the device has not been positioned properly, prompting the operator to further advance the tether-cutting device before completing the actuation of the cutting blade to cut the tether.

The operator may control the operation of the device using the proximal handle. After the tether has been loaded into the tether-cutting device, the operator may then use one or more actuation mechanisms in the proximal handle to cut the tether. For example, the operator may move an actuation mechanism that controls the movement of the cutting blade to advance the blade within the lumen of the catheter and cut the tether. In the variation depicted in FIG. 6, the operator may control an actuation mechanism that rotates and translates the cutting blade within a lumen of the catheter. In another variation, the operator may control separate actuation mechanisms to control rotation and translation of the cutting blade. In order to move the cutting blade using the actuation mechanism, the operator may need to deactivate a mechanism designed to hold the cutting blade stationary within the lumen of the catheter. For example, the operator may need to remove a safety tab inserted into the proximal handle and coupled to the actuation mechanism in order to move the cutting blade. In another variation, the operator may remove a safety tab coupled to the cutting blade and/or a lead screw. In a further variation, the operator may merely turn or move a safety tab rather than fully removing it from the proximal handle. After the operator has moved the cutting blade, the operator may replace the mechanism used to hold the blade stationary. For example, after the operator has cut the tether, the operator may use the safety tab to maintain the blade in a stationary position within the lumen of the catheter while the device is extracted from the subject. In one variation, the cutting blade may be configured to move both distally and proximally within the lumen of the catheter. The operator may retract the cutting blade by using an actuation mechanism to move the blade distally within the lumen of the catheter. For example, the operator may move the cutting blade proximally by moving the actuation mechanism in one direction, and distally by moving the actuation mechanism in the opposite direction. In another variation, the operator may actuate separate actuation mechanisms in order to move the cutting blade in opposite directions. An advantage of a method in which is operator may move the cutting blade both distally and proximally is that the operator may move the cutting blade proximally in order to reposition the cutting blade within the catheter lumen.

Optionally, some variations may comprise translating the inner shaft to facilitate the cutting of the tether. For example, in variations of the tether-cutting device where the tether-cutting device possesses a moveable inner shaft, the operator may control an actuation mechanism to translate the inner shaft within the lumen of the catheter, e.g., translating the inner shaft distally before actuating the cutting blade. For example, the inner shaft may have a predetermined range of movement, and a retracted position and an extended position within the range. The relative position of the inner shaft and the proximal-most sidewall opening of the catheter may affect the tracking force of the tether by changing the angle (e.g., angle $\alpha_1$) of the tether in the lumen of the catheter. The operator may adjust the angle of the tether, and consequently the tracking force, by moving the inner shaft proximally or distally within the lumen of the catheter. For example, in order to reduce the tracking force, the operator may move the inner shaft proximally into a retracted position within the lumen of the catheter. Reduced tracking force may provide the benefit of making it easier for the operator to advance the catheter over the tether. Optionally, the operator may move the inner shaft distally to an extended position within the lumen of the catheter. Moving the tether distally within the lumen of the catheter may increase portion of the tether that is in the travel path of the cutting blade (i.e., so that a greater length of the tether comes into contact with the blade), which may facilitate cutting of the tether. In order to move the inner shaft using an actuation mechanism, the operator may deactivate a mechanism designed to hold the inner shaft stationary within the lumen of the catheter. For example, the operator may remove a safety tab inserted into the proximal handle and coupled to an actuation mechanism in order to move the inner shaft. In another variation, the operator may remove a safety tab coupled to the cutting blade. In a further variation, the operator may merely turn or move a safety tab rather than fully removing it. The operator may at any point wish to maintain the position of the inner shaft within the lumen of the catheter, such as after the operator has moved the inner shaft to a desired location. The operator may reactivate the safety mechanism to hold the inner shaft stationary, for example, by replacing a safety tab into an opening in the proximal handle of the tether-cutting device. It should also be appreciated that in some variations of a tether-cutting device, the operator will not move the inner shaft.

In some variations, the operator may check if the tether has been successfully cut by the tether-cutting device. For example, the operator may pull on the proximal end of the tether, and evaluate whether the tether has been cut. If the tether can be easily pulled, this may signal to the operator that the tether has been fully cut. If some tension still remains in the tether, this may signal to the operator that the tether has not been fully cut, or has not been cut at all. If the tether has not been completely cut (or cut at all), the operator may retract the cutting blade, apply tension on the tether, and then distally advance the cutting blade a second time. Additionally the operator may remove the cutting blade and/or the inner shaft and/or any actuation mechanisms thereof if they are suspected of being damaged while leaving the catheter in place and replace the removed components (e.g. the cutting blade, inner shaft, and/or actuation mechanisms). This may be desirable, for example, if components of the device are damaged and should be replaced, but the operator would prefer to keep the catheter in place while replacing the inner shaft and/or cutting blade. Because the tether may be threaded through the catheter, leaving the catheter in place while replacing other components of the tether-cutting device may provide the advantage of making the process of replacing components less cumbersome by avoiding the need to re-thread the tether through the catheter. After the operator has confirmed that the tether has been successfully cut, the operator may retract the tether-cutting device from the target site of the subject. The operator may use the proximal handle to pull the catheter assembly away from the target site and out of the subject. Prior to retracting the device, the operator may wish to ensure that some elements of the catheter assembly, such as the cutting blade and the inner shaft, remain stationary within the catheter. As discussed above, the operator may utilize mechanisms, such as safety tabs, to hold the cutting blade and/or inner shaft in place while the device is retracted.

Some variations of methods described herein may comprise introducing fluids or devices into the lumen of the catheter, the inner shaft, or the cutting blade. The proximal handle of the tether-cutting device may comprise various ports to allow the operator to introduce devices and/or substances into the tether-cutting device. An outer port in fluid communication with the catheter lumen, an inner port in fluid communication with the inner shaft lumen, and a cutter port in fluid communication with the cutting blade lumen may allow the operator to introduce fluids into the catheter, the inner shaft, and the cutting blade, respectively. For example, the operator may introduce fluids such as saline solution, contrast agents, medicaments, or any suitable liquid into any component of the tether-cutting device. The operator may also introduce one or more devices, such as implant delivery devices, catheters, imaging devices, or any other suitable device into any component of the tether-cutting device through the various ports.

While various inventive variations have been described and illustrated herein, a variety of other means and/or structures may be used for performing the function and/or obtaining the results and/or one or more of the advantages described herein, and each of such variations and/or modifications is deemed to be within the scope of the inventive variations described herein. More generally, all parameters, dimensions, materials, and configurations described herein are meant to be exemplary and that the actual parameters, dimensions, materials, and/or configurations will depend upon the specific application or applications for which the inventive teachings is/are used. There are many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A tether-cutting device comprising:
    a catheter comprising a proximal end, a distal end, a lumen therethrough, and a sidewall, wherein the sidewall comprises a first opening and a second opening distal to the first opening;
    an inner shaft comprising a proximal end, a distal end, and a shaft lumen therethrough, wherein the inner shaft is disposed within the lumen of the catheter proximal to the first opening;
    a cutting blade disposed over the inner shaft; and
    an actuation mechanism coupled to the cutting blade configured to rotate and translate the cutting blade about the inner shaft.

2. The device of claim 1, wherein the inner shaft is stationary within the lumen of the catheter.

3. The device of claim 1, wherein the inner shaft is moveable within the lumen of the catheter.

4. The device of claim 3, further comprising a lead screw coupled to the inner shaft, wherein rotation of the lead screw translates the inner shaft.

5. The device of claim 4, further comprising an actuation mechanism coupled to the lead screw such that moving the actuation mechanism turns the lead screw.

6. The device of claim 3, further comprising a gear mechanism coupled to the inner shaft, wherein rotation of the gear translates the inner shaft.

7. The device of claim 1, further comprising a first configuration wherein a distal end of the blade is proximal to the distal end of the inner shaft, and a second configuration wherein the distal end of the blade is distal to the distal end of the inner shaft.

8. The device of claim 3, wherein the actuation mechanism is configured to move the blade between the first and second configurations in order to cut a tether.

9. The device of claim 1, wherein the distal end of the inner shaft is blunt.

10. The device of claim 1, wherein the blade is tubular.

11. The device of claim 1, wherein the inner shaft is coaxial with the blade.

12. The device of claim 1, further comprising a proximal handle.

13. The device of claim 8, wherein the handle comprises the actuation mechanism.

14. The device of claim 1, wherein the actuation mechanism comprises a lead screw coupled to the blade wherein rotation of the screw rotates and longitudinally translates the blade.

15. The device of claim 9, wherein the actuation mechanism is configured to simultaneously slide the blade along a length of the catheter, and rotate the blade about a longitudinal axis of the catheter.

16. The device of claim 9, wherein the actuation mechanism is configured to bidirectionally move the blade distally and proximally within the catheter.

17. The device of claim 9, wherein the blade is retained within the lumen of the catheter by the actuation mechanism.

18. The device of claim 1, wherein the lumen of the catheter terminates at a distal opening.

19. The device of claim 1, wherein a tether extending from the second opening, through the first opening, and through the shaft lumen extends partially across the lumen of the catheter.

20. A method of cutting a catheter comprising:
    advancing a tether-cutting device over a tether, wherein the tether-cutting device comprises:
        a catheter comprising a lumen and a sidewall, wherein the sidewall comprises a first opening, and a second opening distal to the first opening;
        an inner shaft comprising a shaft lumen, wherein the inner shaft is disposed within the lumen of the catheter;
        and a cutting blade disposed over the inner shaft;
    and wherein the tether extends from the second opening, through the first opening, and through the shaft lumen such that a portion of the tether extends partially across the lumen of the catheter;
    applying tension to the tether; and
    simultaneously rotating and distally translating the blade to cut the portion of the tether that extends partially across the lumen of the catheter.

21. The method of claim 20, wherein rotating and distally translating the blade comprises actuating an actuation mechanism coupled to the cutting blade.

22. The method of claim 21, wherein the actuation mechanism is in a proximal handle.

23. The method of claim 20, furthering comprising actuating the blade to move from a first position in which a distal end of the blade is proximal to a distal end of the inner shaft, to a second position in which the distal end of the blade is distal to the distal end of the inner shaft.

24. The method of claim 20, wherein simultaneously rotating and distally translating the blade comprises moving the blade from the first position to the second position.

25. The method of claim 23, wherein the blade remains in the first position until actuated using the actuation mechanism.

26. The method of claim 20, wherein the blade and the inner shaft are coaxial.

27. The method of claim 20, wherein the tether is a component of a heart implant that has been secured in a heart at an implant site, and wherein the method further comprises advancing the tether-cutting device to the implant site.

28. The method of claim 27, wherein the implant is a valve repair device comprising anchors affixed to tissue and coupled to the tether.

29. The method of claim 20, further comprising proximally translating the blade.

30. The method of claim 20, wherein a length of a tether that extends from the first opening into the shaft lumen forms an angle with respect to a longitudinal axis of the shaft lumen, and wherein the method further comprises adjusting the angle to a first pre-selected angle prior to advancing the tether-cutting device over the tether and adjusting the angle to a second pre-selected angle prior to cutting the tether, wherein the second pre-selected angle is greater than the first pre-selected angle.

31. The method of claim 30, wherein adjusting the angle to the first pre-selected angle comprises proximally translating the inner shaft and adjusting the angle to the second pre-selected angle comprises distally translating the inner shaft.

* * * * *